United States Patent
Kohn et al.

(10) Patent No.: US 9,080,015 B2
(45) Date of Patent: *Jul. 14, 2015

(54) BIOCOMPATIBLE POLYMERS FOR MEDICAL DEVICES

(75) Inventors: Joachim B. Kohn, Piscataway, NJ (US); Durgadas Bolikal, Edison, NJ (US); Ramiro Rojas, Stockholm (SE)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 285 days.

This patent is subject to a terminal disclaimer.

(21) Appl. No.: 13/387,799

(22) PCT Filed: Jul. 31, 2010

(86) PCT No.: PCT/US2010/044050
§ 371 (c)(1), (2), (4) Date: Mar. 30, 2012

(87) PCT Pub. No.: WO2011/014859
PCT Pub. Date: Feb. 3, 2011

(65) Prior Publication Data
US 2012/0178885 A1    Jul. 12, 2012

Related U.S. Application Data

(60) Provisional application No. 61/230,558, filed on Jul. 31, 2009.

(51) Int. Cl.
| | |
|---|---|
| *A61K 47/34* | (2006.01) |
| *C08G 67/00* | (2006.01) |
| *C08G 69/44* | (2006.01) |
| *C08G 69/48* | (2006.01) |
| *C08G 79/02* | (2006.01) |
| *A61K 47/48* | (2006.01) |

(52) U.S. Cl.
CPC .......... *C08G 79/02* (2013.01); *A61K 47/48192* (2013.01); *A61K 47/48215* (2013.01); *C08G 79/025* (2013.01)

(58) Field of Classification Search
CPC ................. A61K 47/48192; A61K 47/48215; C08G 79/02; C08G 79/025
USPC ........................................... 528/86, 211, 374
See application file for complete search history.

(56) References Cited

U.S. PATENT DOCUMENTS

| | | |
|---|---|---|
| 3,636,956 A | 1/1972 | Schneider |
| 3,663,515 A | 5/1972 | Hostettler et al. |
| 4,744,365 A | 5/1988 | Kaplan et al. |
| 4,747,956 A | 5/1988 | Kiniwa |
| 4,822,829 A | 4/1989 | Muller et al. |
| 4,980,449 A | 12/1990 | Kohn et al. |
| 5,003,004 A | 3/1991 | Simms |
| 5,066,772 A | 11/1991 | Tang et al. |
| 5,099,060 A | 3/1992 | Kohn et al. |
| 5,216,115 A | 6/1993 | Kohn et al. |
| 5,219,564 A | 6/1993 | Zalipsky et al. |
| 5,403,347 A | 4/1995 | Roby et al. |
| 5,431,679 A | 7/1995 | Bennett et al. |
| 5,587,507 A | 12/1996 | Kohn et al. |
| 5,660,822 A | 8/1997 | Poiani et al. |
| 5,665,831 A | 9/1997 | Neuenschwander et al. |
| 5,670,602 A | 9/1997 | Kohn et al. |
| 5,702,717 A | 12/1997 | Cha et al. |
| 5,854,383 A | 12/1998 | Erneta et al. |
| 5,916,998 A | 6/1999 | Ferruti et al. |
| 5,952,450 A | 9/1999 | Ishihara et al. |
| 6,120,491 A | 9/2000 | Kohn et al. |

(Continued)

FOREIGN PATENT DOCUMENTS

| | | |
|---|---|---|
| JP | 2004-513971 | 5/2004 |
| WO | 9836013 A1 | 8/1998 |
| WO | 2007/018544 A2 | 2/2007 |
| WO | 2007/143698 | 12/2007 |
| WO | 2008/082738 A2 | 7/2008 |

OTHER PUBLICATIONS

Nathan et al., Bio. Cong. Chem., 4, 54-62 (1993).
Nathan, Macromol., 25, 4476 (1992).
Teng et al., "Synthesis and characterization of poly(L-lactic acid)-poly(e-caprolactone) multiblock copolymers by melt polycondensation," Journal of Polymer Science Part A: Polymer Chemistry. 42: pp. 5045-5053, 2004. (Abstract).
Mligiliche et al., ,"Poly lactic acid-caprolactone copolymer tube with a denatured skeletal muscle segment inside as a guide for peripheral nerve regeneration: A morphological and electrophysiological evaluation of the regenerated nerves," Anatomical Science International, vol. 78, No. 3, Sep. 2003, pp. 156-161. (Abstract).

(Continued)

*Primary Examiner* — Richard Schnizer
*Assistant Examiner* — Alma Pipic
(74) *Attorney, Agent, or Firm* — Fox Rothschild LLP

(57) ABSTRACT

The present invention relates to new classes of biocompatible polymers comprising at least one repeating unit derived from a compound of Formula (I) as defined in the claims and specification. These polymers may be biodegradable and bioresorble, and, while not limited thereto, may be adapted for radio-opacity and are useful for medical device applications and controlled release therapeutic formulations. Therefore, methods for preparing these polymers and medical devices prepared therefrom are also encompassed by this disclosure.

(I)

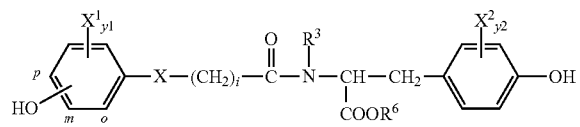

14 Claims, No Drawings

(56) References Cited

U.S. PATENT DOCUMENTS

| | | |
|---|---|---|
| 6,228,969 B1 | 5/2001 | Lee et al. |
| 6,316,585 B1 | 11/2001 | Lele et al. |
| 6,355,754 B1 | 3/2002 | Olson et al. |
| 6,475,477 B1 | 11/2002 | Kohn et al. |
| 6,592,899 B2 | 7/2003 | Fowers et al. |
| 6,602,497 B1 | 8/2003 | Kohn et al. |
| 6,943,214 B2 | 9/2005 | Flexman |
| 7,166,134 B2 | 1/2007 | Datta et al. |
| 7,169,187 B2 | 1/2007 | Datta et al. |
| 7,479,157 B2 | 1/2009 | Weber et al. |
| 2001/0046505 A1 | 11/2001 | Kohn et al. |
| 2004/0082734 A1 | 4/2004 | Hatton et al. |
| 2005/0106119 A1 | 5/2005 | Brandom et al. |
| 2006/0024266 A1 | 2/2006 | Brandom et al. |
| 2006/0034769 A1 | 2/2006 | Kohn et al. |
| 2006/0034891 A1 | 2/2006 | Lawin et al. |
| 2006/0036316 A1 | 2/2006 | Zeltinger et al. |
| 2006/0178477 A1 | 8/2006 | Neuenschwander |
| 2007/0117959 A1 | 5/2007 | Shastri et al. |
| 2007/0190151 A1 | 8/2007 | Chai et al. |
| 2007/0231365 A1 | 10/2007 | Wang et al. |
| 2007/0282435 A1 | 12/2007 | Wang et al. |
| 2008/0063685 A1 | 3/2008 | Wang et al. |
| 2008/0112999 A1 | 5/2008 | Baluca |
| 2008/0146504 A1 | 6/2008 | Bonnin |
| 2008/0152690 A1 | 6/2008 | Kohn et al. |
| 2008/0187567 A1 | 8/2008 | Kohn et al. |
| 2008/0243049 A1 | 10/2008 | Hardy |
| 2008/0243228 A1 | 10/2008 | Wang et al. |
| 2008/0269874 A1 | 10/2008 | Wang et al. |
| 2009/0004243 A1 | 1/2009 | Pacetti et al. |
| 2009/0035350 A1 | 2/2009 | Stankus et al. |
| 2009/0088835 A1 | 4/2009 | Wang |

OTHER PUBLICATIONS

Sousa, A., et al., "Selective Protein Adsorption on a Phase-Separated Solvent-Cast Polymer Blend", Langmuir, 22, 2006, pp. 6286-6292.

Tangpasuthadol, V., et al., "Thermal properties and physical ageing behaviour of tyrosine-derived polycarbonates", Biomaterials, 1996, vol. 17, No. 4., pp. 463-468.

Sakar, D., et al., Structure-Property Relationship of L-Tyrosine-Based Polyurethanes for Biomaterial Applications, Journal of Applied Polymer Science, vol. 108, 23435-2355 (2008).

Polycarprolactone diol, 2011 obtained from the Sigma-Aldrich website: (http://www.sigmaaldrich.com/catalog/ProductDetail.do?D7=0&N5=SEARCH_CONCAT_PNO%7CBRAND_KEY&N4=189421%7CALDRICH&N25=0&QS=ON&F=SPEC).

Dobrzynski et al. Structure-Property Relationships of Copolymers Obtained by Ring-Opening Polymerization of Glycolide and e-Caprolactone. Part 1. Synthesis and Characterization. Biomacromolecules 6(1): 483-488. 2005.

Latham, K. et al., "Development of Support Matrices for Affinity Chromatography of Thyroid Hormone Receptors," The J. of Biological Chem, Dec. 10, 1981, vol. 256, pp. 12088-12093.

Perez, P. et al., "Bioresorbable and Nonresorbable Macroporous Thermosensitive Hydrogels Prepared by Cryopolymerization. Role of the Cross-Linking Agent," Biomacromolecules 2008, vol. 9, pp. 66-74.

Tang, S. et al., "Synthesis and Characterization of Water-Soluble and Photostable L-Dopa Dendrimers," Organic Letters, 2006, vol. 8, No. 20, pp. 4421-4424.

Kalgutkar, A. S. et al., "Design, Synthesis, and Biochemical Evaluation of N-Substituted Maleimides as Inhibotors of Prostaglandin Endoperoxid Synthesis," J. Med. Chem., 1996, vol. 39, pp. 1692-1703 (Abstract).

Kakemi K. et al., "Studies on the Pharmaceutical Potential of Drugs. I. p-Aminosalicylic Acid Derivatives," Chemical & Pharmaceutical Bulletin, 1967, vol. 15(12), pp. 1819-1827 (Abstract).

BIOCOMPATIBLE POLYMERS FOR MEDICAL DEVICES

CROSS-REFERENCE TO RELATED APPLICATIONS

This application is the U.S. National Phase of International Patent Application Serial No. PCT/US10/44050, filed on Jul. 31, 2010, which claims priority under 35 U.S.C. §119(e) to U.S. Provisional Patent Application Ser. No. 61/230,558, filed on Jul. 31, 2009, both of which are hereby incorporated by reference in their entireties for all purposes.

STATEMENT REGARDING FEDERALLY SPONSORED RESEARCH

The invention described herein was supported in whole or in part by grants from the National Institutes of Health (Grant No. EB001046). The U.S. Government has certain rights in this invention.

FIELD OF THE INVENTION

The present invention relates to new classes of monomeric compounds, which may be polymerized to form novel biodegradable and bioresorble polymers and co-polymers. These polymers and co-polymers, while not limited thereto, may be adapted for radio-opacity and are useful for medical device applications and controlled release therapeutic formulations.

The present invention thus also relates to new biocompatible polymers suitable for use in implantable medical devices and monomers for such polymers. In particular, the present invention relates to polymers polymerized from monomer analogs of compounds that naturally occur in the human body and that contribute advantageous synthesis, processing and material properties to the polymers prepared therefrom.

BACKGROUND OF THE INVENTION

Diphenols are monomeric starting materials for polycarbonates, polyiminocarbonates, polyarylates, polyurethanes and the like. Commonly owned U.S. Pat. No. 5,099,060 discloses diphenolic monomers based on 3-(4-hydroxyphenyl) propionic acid and L-tyrosine alkyl esters (desaminotyrosyl-tyrosine alkyl esters). Subsequent related patents involve variations of this basic monomer structure, including halogenated radiopaque diphenolic monomers, such as the 3,5-diiododesaminotyrosyl-tyrosine esters ($I_2$DTX, wherein X=ester group, e.g., E=ethyl, H=hexyl, O=octyl, etc.) disclosed by U.S. Patent Application Publication No. 2006/0034769. The disclosures of both publications are incorporated by reference. Examples of other polymers suitable for various bioengineering applications include those described in U.S. Pat. No. 5,665,831; U.S. Pat. No. 5,916,998 and U.S. Pat. No. 6,475,477, along with the polymers described in U.S. Pat. Publication No. 2006/0024266, the disclosures of all of which are also incorporated by reference.

Although these monomers are useful in the synthesis of polymers for many medical implant applications, the rapidly evolving field of bioengineering has created a demand for a diverse library of different types of polymers offering a wide variety of choice of physical and mechanical properties. It is desirable that libraries of many different materials be available so that the specific polymer properties can be optimally matched with the requirements of the specific applications under development.

SUMMARY OF THE INVENTION

The present invention addresses these needs. Various embodiments provide polymer compositions derived from new monomers, medical devices containing such compositions, and methods of using such polymer compositions and devices.

New classes of monomeric compounds are provided, which may be polymerized to form novel polymers and co-polymers that, while not limited thereto, may be adapted for radio-opacity and are useful for medical device applications and controlled release therapeutic formulations, although not limited thereto. More specifically, the present invention introduces a novel class of monomers, which are polymerized to form polymers and copolymers with at least one or more aromatic repeating units that are analogs of compounds that naturally occur in the human body.

In one aspect the present invention provides new monomers having a structure of Formula (I):

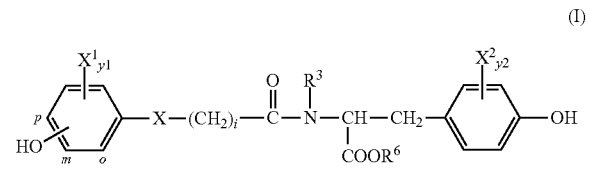

(I)

wherein:

i is an integer selected from 1 through 4;

$y^1$ and $y^2$ are each independently selected from 0, 1, 2, 3 and 4;

$X^1$ and $X^2$, at each occurrence, are independently bromine (Br) or iodine (I);

X is oxygen (O), sulfur (S), or $NR^4$; where $R^4$ is selected from the group consisting of hydrogen and alkyl containing from 1 to 6 carbon atoms $R^3$ is an optionally substituted $C_{1-30}$ alkyl; and $R^6$ is hydrogen or an alkyl, aryl, alkylaryl, heteroalkyl or heteroalkylaryl group containing up to 30 carbon atoms, wherein the heteroalkyl group contains from 1 to 10 heteroatoms independently selected from O, $NR^3$ and S and the heteroalkylaryl group contains from 1 to 3 heteroatoms independently selected from O, $NR^3$ and S;

wherein the —$X^1$ and —OH groups on the left phenyl ring, at each occurrence, are independently at o-, m-, or p-positions.

In one aspect the present invention provides a biocompatible polymer comprising:

a first repeating unit of Formula (Ia):

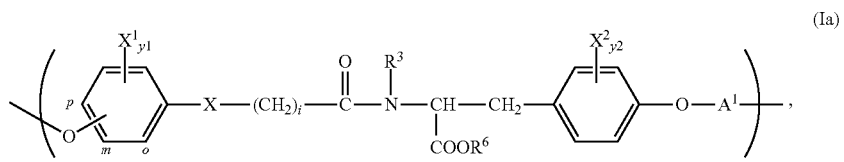

(Ia)

wherein:
i is an integer selected from 1 through 4;
$y^1$ and $y^2$ are each independently selected from 0, 1, 2, 3 and 4;
$X^1$ and $X^2$, at each occurrence, are independently bromine (Br) or iodine (I);
X is oxygen (O), sulfur (S), or $NR^4$; where $R^4$ is selected from the group consisting of hydrogen and alkyl containing from 1 to 6 carbon atoms
$R^3$ is an optionally substituted $C_{1-30}$ alkyl;
$R^6$ is hydrogen or an alkyl, aryl, alkylaryl, heteroalkyl or heteroalkylaryl group containing up to 30 carbon atoms, wherein the heteroalkyl group contains from 1 to 10 heteroatoms independently selected from O, $NR^3$ and S and the heteroalkylaryl group contains from 1 to 3 heteroatoms independently selected from O, $NR^3$ and S; and
$A^1$ at each occurrence is independently selected from:
a bond,

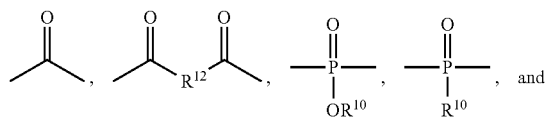

-continued

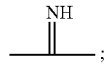

$R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkyl, alkenyl or alkynyl, $C_1$-$C_{30}$ heteroalkyl; heteroalkenyl or heteroalkynyl, $C_5$-$C_{30}$ heteroalkylaryl, heteroalkenylary or heteroalkynylaryl, $C_6$-$C_{30}$ alkylaryl, alkenylaryl or alkynylaryl, and $C_5$-$C_{30}$ heteroaryl;

wherein the —$X^1$ and —O— groups on the left phenyl ring, at each occurrence, are independently at o-, m-, or p-positions; and a second repeating unit of Formula (IIa):

(IIa)

wherein:
$X_1$ and $X_2$ are independently selected from the group consisting of O, S and $NR_3$, wherein $R_3$ is selected from the group consisting of hydrogen and alkyl groups containing from one to 30 carbon atoms;

$Ar_1$ selected from the group consisting of phenyl,

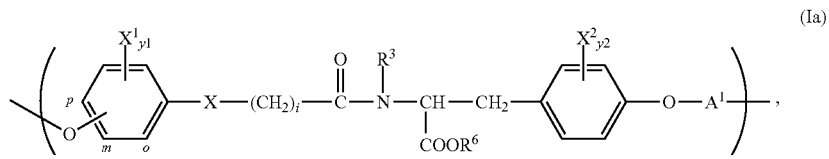

optionally substituted with from one to four substituents independently selected from the group consisting of halogen, halomethyl, halo-methoxy, methyl, methoxy, thiomethyl, nitro, sulfoxide and sulfonyl; and $R_1$ is selected from the group consisting of an optionally substituted alkyl, heteroalkyl, alkenyl and heteroalkenyl groups containing from one to ten carbon atoms.

In another aspect the present invention provides a biocompatible polymer comprising:

a first repeating unit of Formula (Ia):

(Ia)

wherein:
i is an integer selected from 1 through 4;
$y^1$ and $y^2$ are each independently selected from 0, 1, 2, 3 and 4;
$X^1$ and $X^2$, at each occurrence, are independently bromine (Br) or iodine (I);
X is oxygen (O), sulfur (S), or $NR^4$; where $R^4$ is selected from the group consisting of hydrogen and alkyl containing from 1 to 6 carbon atoms
$R^3$ is an optionally substituted $C_{1-30}$ alkyl;
$R^6$ is hydrogen or an alkyl, aryl, alkylaryl, heteroalkyl or heteroalkylaryl group containing up to 30 carbon atoms, wherein the heteroalkyl group contains from 1 to 10 heteroatoms independently selected from O, $NR^3$ and S and the heteroalkylaryl group contains from 1 to 3 heteroatoms independently selected from O, $NR^3$ and S; and
$A^1$ at each occurrence is independently selected from:
a bond,

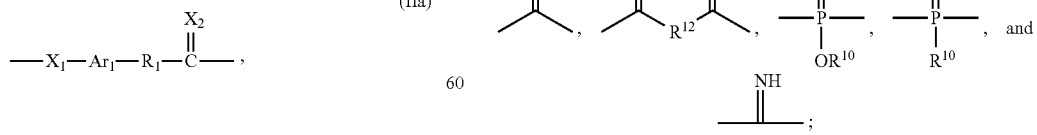

$R^{10}$ is selected from H, $C_1$-$C_{30}$ alkyl, alkenyl or alkynyl and $C_2$-$C_{30}$ heteroalkyl; heteroalkenyl or heteroalkynyl; and
$R^{12}$ is selected from $C_1$-$C_{30}$ alkyl, alkenyl or alkynyl, $C_1$-$C_{30}$ heteroalkyl; heteroalkenyl or heteroalkynyl, $C_5$-$C_{30}$ heteroalkylaryl, heteroalkenylary or heteroalkynylaryl, $C_6$-$C_{30}$ alkylaryl, alkenylaryl or alkynylaryl, and $C_5$-$C_{30}$ heteroaryl;

wherein the —$X^1$ and —O— groups on the left phenyl ring, at each occurrence, are independently at o-, m-, or p-positions; and a second repeating unit of Formula (IIIa):

$$—X_1—\overset{X_2}{\overset{\|}{C}}—R_1—Ar_1—X_3—B_1—X_4—Ar_2—R_2—\overset{X_5}{\overset{\|}{C}}—X_6—, \quad (IIIa)$$

wherein:

$X_1, X_2, X_3, X_4, X_5,$ and $X_6$ are independently selected from the group consisting of O, S and $NR_3$ wherein $R_3$ is selected from the group consisting of hydrogen and alkyl groups containing from 1 to 30 carbon atoms;

$Ar_1$ and $Ar_2$ are independently selected from the group consisting of phenyl,

[structure: diphenyl ether and 5-methylindole groups] and optionally substituted with from one to four substituents independently selected from the group consisting of halogen, halomethyl, halomethoxy, methyl, methoxy, thiomethyl, nitro, sulfoxide, and sulfonyl;

$R_1$ and $R_2$ are independently selected from the group consisting of an optionally substituted alkyl, heteroalkyl, alkenyl and heteroalkenyl groups containing from one to ten carbon atoms; and $B_1$ is a carbonyl group.

In another aspect the present invention provides a biocompatible polymer comprising:

a first repeating unit of Formula (Ia):

$$\left(\begin{array}{c}\text{[structure Ia]}\end{array}\right) \quad (Ia)$$

wherein:

i is an integer selected from 1 through 4;

$y^1$ and $y^2$ are each independently selected from 0, 1, 2, 3 and 4;

$X^1$ and $X^2$, at each occurrence, are independently bromine (Br) or iodine (I);

X is oxygen (O), sulfur (S), or $NR^4$; where $R^4$ is selected from the group consisting of hydrogen and alkyl containing from 1 to 6 carbon atoms $R^3$ is an optionally substituted $C_{1-30}$ alkyl; and $R^6$ is hydrogen or an alkyl, aryl, alkylaryl, heteroalkyl or heteroalkylaryl group containing up to 30 carbon atoms, wherein the heteroalkyl group contains from 1 to 10 heteroatoms independently selected from O, $NR^3$ and S and the heteroalkylaryl group contains from 1 to 3 heteroatoms independently selected from O, $NR^3$ and S;

wherein the —$X^1$ and —O— groups on the left phenyl ring, at each occurrence, are independently at o-, m-, or p-positions; and a second repeating unit of Formula (IVa):

$$—X_1—Ar_1—R_1—\overset{X_2}{\overset{\|}{C}}—X_3—B—X_4—[\overset{X_5}{\overset{\|}{C}}—R_2—Ar_2—X_6]_f—A^1—, \quad (IVa)$$

wherein:

f is 0 or 1;

$X_1, X_2, X_3, X_4, X_5,$ and $X_6$ are independently selected from the group consisting of O, S and $NR_3$ wherein $R_3$ is selected from the group consisting of hydrogen and alkyl groups containing from 1 to 30 carbon atoms;

$Ar_1$ and $Ar_2$ are independently selected from the group consisting of phenyl,

[structure: diphenyl ether and 5-methylindole groups] and optionally substituted with from one to four substituents independently selected from the group consisting of halogen, halo-methyl, halomethoxy, methyl, methoxy, thiomethyl, nitro, sulfoxide, and sulfonyl;

R1 and R2 are independently selected from the group consisting of an optionally substituted alkyl, heteroalkyl, alkenyl and heteroalkenyl groups containing from one to ten carbon atoms;

B is selected from the group consisting of a carbonyl group and a group having the structure:

$$—\overset{X_7}{\overset{\|}{C}}—B_2—\overset{X_8}{\overset{\|}{C}}—$$

wherein $B_2$ is selected from the group consisting of an optionally substituted alkyl group, an optionally substituted heteroalkyl group, an optionally substituted alkenyl group and an optionally substituted heteroalkenyl group, or $B_2, X_3, X_4, X_7$ and $X_8$ are selected so that

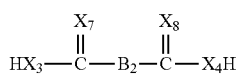

defines a capped macromer structure; and $A^1$ at each occurrence is independently selected from: a bond,

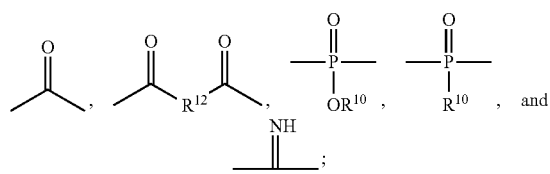

$R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkyl, alkenyl or alkynyl, $C_1$-$C_{30}$ heteroalkyl; heteroalkenyl or heteroalkynyl, $C_5$-$C_{30}$ heteroalkylaryl, heteroalkenylary or heteroalkynylaryl, $C_6$-$C_{30}$ alkylaryl, alkenylaryl or alkynylaryl, and $C_5$-$C_{30}$ heteroaryl.

In another aspect the present invention provides medical devices comprising polymers disclosed herein, which are well-suited for use in producing a variety of resorbable medical devices or other implantable devices. Representative device embodiments include stents, disks, plugs, sutures, staples, clips, surgical adhesives, screws, anchors and the like. These and other similar implantable medical devices are preferably radiopaque, biocompatible, and have various times of bioresorption. To this end, the polymers may be further suitable for use in resorbable implantable devices with and without therapeutic agents, device components and/or coatings with and without therapeutic agents for use in other medical systems.

Other resorbable devices that can be advantageously formed from the polymers disclosed herein, and which serve as representative embodiments of useful medical devices, include devices for use in tissue engineering, dental applications, embolotherapy products for the temporary and therapeutic restriction or blocking of blood supply to treat tumors and vascular malformations, and controlled release therapeutic agent delivery devices, as discussed herein.

In another aspect the present invention provides a method of treating a body lumen, by deploying within the body lumen a stent according to a medical device embodiment of the present invention.

Based on the foregoing, additional embodiments of the compounds, monomers, and polymers of the present invention are discussed herein and will be apparent to one of ordinary skill in the art.

DETAILED DESCRIPTION OF THE INVENTION

Novel classes of compounds, monomers, polymers and co-polymers are provided, polymerized from at least one or more repeatable units of an aromatic compound, which include compounds and analogs of compounds that naturally occur in the human body.

Abbreviations and Nomenclature

The following paragraphs provide definitions of various terms used herein:

As used herein, the terms "macromer," "macromeric" and similar terms have the usual meaning known to those skilled in the art and thus may be used to refer to oligomeric and polymeric materials that are functionalized with end groups that are selected so that the macromers can be copolymerized with other monomers. A wide variety of macromers and methods for making them are known to those skilled in the art. Examples of suitable macromers include hydroxy endcapped polylactic acid macromers, hydroxy endcapped polyglycolic acid macromers, hydroxy endcapped poly(lactic acid-co-glycolic acid) macromers, hydroxy endcapped polycaprolactone macromers, poly(alkylene diol) macromers, hydroxy endcapped poly(alkylene oxide) macromers and hydroxy endcapped polydioxanone macromers.

As used herein, the terms "polymer," "polymeric" and similar terms have the usual meaning known to those skilled in the art and thus may be used to refer to homopolymers, copolymers (e.g., random copolymer, alternating copolymer, block copolymer, graft copolymer) and mixtures thereof.

The term "thermal transition temperature" has the usual meaning known to those skilled in the art and thus may be used to refer to both first order thermal transitions and second order thermal transitions. The first order thermal transition of a polymer or phase thereof may be referred to herein as a "melting point" or Tm", and the second order thermal transition of a polymer or phase thereof may be referred to herein as a "glass transition temperature" or "Tg." Those skilled in the art will appreciate that a polymeric material or phase thereof may have exhibit either or both types of thermal transitions, as well as higher order thermal transitions. Thermal transition temperature may be determined by methods known to those skilled in the art, such as by DSC, DMA, DEA and TMA.

As used herein, the phrase "fracture toughness" means the resistance of a polymer under a static or dynamic load (or strain) to brittle failure from crack propagation within a glassy or semicrystalline phase.

The terms "radiopaque," "radio-opaque," "radiopacity," "radio-opacity," "radiopacifying" and similar terms have the usual meaning known to those skilled in the art and thus may be used to refer to polymer compositions that have been rendered easier to detect using medical imaging techniques (e.g., by X-ray and/or during fluoroscopy) being the incorporation of heavy atoms into the polymer composition. Such incorporation may be by mixing, e.g., by mixing an effective amount of a radiopacifying additive such as barium salt or complex, and/or by attachment of effective amounts of heavy atoms to one or more of the polymers in the polymer composition. For example, attachment of heavy atoms to a polymer in sufficient amounts may advantageously render the polymer easier to detect by various medical imaging techniques. The term "heavy atom" is used herein to refer to atoms having an atomic number of 17 or greater. Preferred heavy atoms have an atomic number of 35 or greater, and include bromine, iodine, bismuth, gold, platinum tantalum, tungsten, and barium. In certain configurations, polymer compositions may be inherently radiopaque. The term "inherently radiopaque" is used herein to refer to a polymer to which a sufficient number of heavy atoms are attached by covalent or ionic bonds to render the polymer radiopaque. This meaning is consistent with the under-standing of those skilled in the art, see, e.g., U.S. Patent Publication No. 2006/0024266, which is hereby incorporated by reference for all purposes, including for the particular purpose of describing radiopaque polymeric materials.

The terms "alkyl", "alkylene" and similar terms have the usual meaning known to those skilled in the art and thus may be used to refer to straight or branched hydrocarbon chain fully saturated (no double or triple bonds) hydrocarbon group. Terminal alkyl groups, e.g., of the general formula —$C_nH_{2n+1}$, may be referred to herein as "alkyl" groups, whereas linking alkyl groups, e.g., of the general formula —$(CH_2)_n$—, may be referred to herein as "alkylene" groups. The alkyl group may have 1 to 50 carbon atoms (whenever it appears herein, a numerical range such as "1 to 50" refers to each integer in the given range; e.g., "1 to 50 carbon atoms" means that the alkyl group may consist of 1 carbon atom, 2 carbon atoms, 3 carbon atoms, etc., up to and including 50 carbon atoms, although the present definition also covers the occurrence of the term "alkyl" where no numerical range is designated). The alkyl group may also be a medium size alkyl having 1 to 30 carbon atoms. The alkyl group could also be a lower alkyl having 1 to 5 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl and the like.

The alkyl group may be substituted or unsubstituted. When substituted, the substituent group(s) is(are) one or more group(s) individually and independently selected from lower alkyl, alkenyl, alkynyl, cycloalkyl, cycloalkenyl, cycloalkynyl, aryl, hydroxyaryl, heteroaryl, heteroalicyclyl, aralkyl, heteroaralkyl, (heteroalicyclyl)alkyl, hydroxy, protected hydroxyl, alkoxy, aryloxy, acyl, carboxyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

The terms "alkenyl," "alkenylene" and similar terms have the usual meaning known to those skilled in the art and thus may be used to refer to an alkyl or alkylene group that contains in the straight or branched hydrocarbon chain one or more double bonds. An alkenyl group may be unsubstituted or substituted. When substituted the substituent(s) may be selected from the same groups disclosed above with regard to alkyl group substitution unless otherwise indicated.

The terms "heteroalkyl," "heteroalkylene" and similar terms have the usual meaning known to those skilled in the art and thus may be used to refer to an alkyl group or alkylene group as described herein in which one or more of the carbons atoms in the backbone of alkyl group or alkylene group has been replaced by a heteroatom such as nitrogen, sulfur and/or oxygen. Likewise, the term "heteroalkenylene" may be used to refer to an alkenyl or alkenylene group in which one or more of the carbons atoms in the backbone of alkyl group or alkylene group has been replaced by a heteroatom such as nitrogen, sulfur and/or oxygen.

The term "aryl" has the usual meaning known to those skilled in the art and thus may be used to refer to a carbocyclic (all carbon) monocyclic or multicyclic aromatic ring system that has a fully delocalized pi-electron system. Examples of aryl groups include, but are not limited to, benzene, naphthalene and azulene. The ring of the aryl group may have 5 to 50 carbon atoms. The aryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfon-amido, and amino, including mono- and di-substituted amino groups, and the protected derivatives thereof, unless the substituent groups are otherwise indicated. An aryl group substituted with alkyl may be referred to herein as "alkylaryl."

The term "heteroaryl" has the usual meaning known to those skilled in the art and thus may be used to refer to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The ring of the heteroaryl group may have 5 to 50 atoms. The heteroaryl group may be substituted or unsubstituted. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thia-diazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

The term "crystallizable" has the usual meaning known to those skilled in the art, see U.S. Patent Publication No. 20060024266, which is incorporated herein by reference for all purposes and particularly for the purpose of describing crystallizable groups. Polymers that contain crystallizable groups that are attached to the sides of the polymer, known as side chain crystallizable (SCC) polymers or "comb-like" polymers, are well-known, see N. A. Plate and V. P. Shibaev, J. Polymer Sci.: Macromol. Rev. 8:117-253 (1974), the disclosure of which is hereby incorporated by reference. In an embodiment, a polymer as described herein contains crystallizable side groups and thus may be regarded as a SCC polymer. It will be understood that the crystallizable side chains of SCC polymers are preferably selected to crystallize with one another to form crystalline regions and may comprise, for example, —$(CH_2)_x$— and/or —$((CH_2)_b$—O—$)_y$ groups. The side chains are preferably linear to facilitate crystallization. For SCC polymers that contain —$(CH_2)_x$— groups in the crystallizable side chain, x is preferably in the range of about 6 to about 30, more preferably in the range of about 20 to about 30. For SCC polymers that contain $((CH_2)_y$—O—$)_x$ groups in the crystallizable side chain, x is preferably in the range of about 6 to about 30 and y is preferably in the range of about 1 to about 8. More preferably, x and y are selected so that the $((CH_2)_y\text{—}O\text{—})_x$ groups contain from about 6 to about 30 carbon atoms, even more preferably from about 20 to about 30 carbon atoms. The spacing between side chains and the length and type of side chain are preferably selected to provide the resulting SCC polymer with a desired melting point. As the spacing between side chains increases, the tendency for the side chains to be crystallizable tends to decrease. Likewise, as the flexibility of the side chains increases the tendency for the side chains to be crystallizable tends to decrease. On the other hand, as the length of the side chains increases, the tendency for the side chains to be crystallizable tends to increase. In many cases, the length of the crystallizable side chain may be in the range of about two times to about ten times the average distance between crystallizable side chains of the SCC polymer.

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents.

Unless otherwise indicated, when a substituent is deemed to be "optionally substituted," or "substituted" it is meant that the substituent is a group that may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Similarly, the term "optionally ring-halogenated" may be used to refer to a group that optionally contains one or more (e.g., one, two, three or four) halogen substituents on the aryl and/or heteroaryl ring. The protecting groups that may form the protective derivatives of the above substituents are known to those of skill in the art and may be found in references such as Greene and Wuts, Protective Groups in Organic Synthesis, 3$^{rd}$ Ed., John Wiley & Sons, New York, N.Y., 1999, which is hereby incorporated by reference in its entirety.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound having one or more double bond(s) generating geometrical isomers that can be defined as E or Z each double bond may independently be E or Z a mixture thereof. Likewise, all tautomeric forms are also intended to be included.

As used herein, the abbreviations for any protective groups, amino acids and other compounds are, unless indicated otherwise, in accord with their common usage, recognized abbreviations, or the IUPAC-IUP Commission on Biochemical Nomenclature (See, Biochem. 11:942-944 (1972)).

Polymer Compositions and Methods

In one aspect the present invention provides novel monomers having the following generic structure (A):

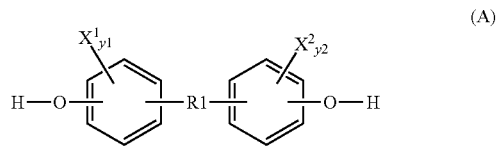

(A)

wherein:

R1 has the structure —$R^2$—C(=O)—$NR^3$—$CHR^4$—$R^5$—; $X^1$ and $X^2$ are bromine or iodine;

and $y^1$ and $y^2$ have values independently selected from 0, 1, 2, 3 and 4;

$R^2$ is a heteroalkyl group containing from one to eight carbon atoms and up to three heteroatoms independently selected from O, $NR^3$ and S;

$R^3$ is hydrogen or a lower alkyl group containing from one to six carbon atoms;

$R^4$ is $COOR^6$, wherein $R^6$ is hydrogen or an alkyl, aryl, alkylaryl, heteroalkyl or heteroalkylaryl group containing up to 30 carbon atoms, wherein the heteroalkyl group contains from 1 to 10 heteroatoms independently selected from O, $NR^3$ and S and the heteroalkylaryl group contains from 1 to 3 heteroatoms independently selected from O, $NR^3$ and S; and $R^5$ is a bond or —$CH_2$—.

Diphenol compounds according to the present invention include compounds in which $R^2$ is —O—$CH^2$—C(=O)— or —$NR^3$—$CH_2$—C(=O)—.

In this aspect the present invention provides new monomers having a structure of Formula (I):

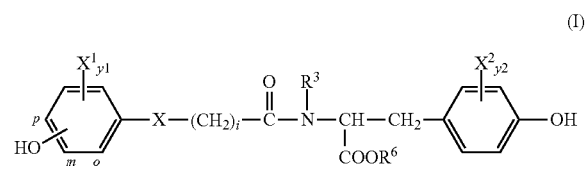

(I)

wherein:

i is an integer selected from 1 through 4;

$y^1$ and $y^2$ are each independently selected from 0, 1, 2, 3 and 4;

$X^1$ and $X^2$, at each occurrence, are independently bromine (Br) or iodine (I);

X is oxygen (O), sulfur (S), or $NR^4$, where $R^4$ is selected from the group consisting of hydrogen and alkyl containing from 1 to 6 carbon atoms;

$R^3$ is an optionally substituted $C_{1-30}$ alkyl; and $R^6$ is hydrogen or an alkyl, aryl, alkylaryl, heteroalkyl or heteroalkylaryl group containing up to 30 carbon atoms, wherein the heteroalkyl group contains from 1 to 10 heteroatoms independently selected from O, $NR^3$ and S and the heteroalkylaryl group contains from 1 to 3 heteroatoms independently selected from O, $NR^3$ and S;

wherein the —$X^1$ and —OH groups on the left phenyl ring, at each occurrence, are independently at o-, m-, or p-positions.

In one aspect the present invention provides a biocompatible polymer comprising:
a first repeating unit of Formula (Ia):

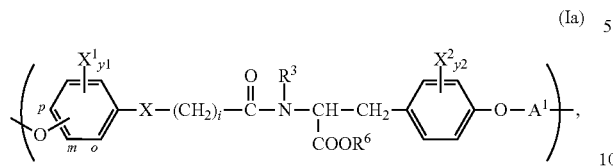

wherein:
i is an integer selected from 1 through 4;
$y^1$ and $y^2$ are each independently selected from 0, 1, 2, 3 and 4;
$X^1$ and $X^2$, at each occurrence, are independently bromine (Br) or iodine (I);
X is oxygen (O), sulfur (S), or $NR^4$, where $R^4$ is selected from the group consisting of hydrogen and alkyl containing from 1 to 6 carbon atoms;
$R^3$ is an optionally substituted $C_{1-30}$ alkyl;
$R^6$ is hydrogen or an alkyl, aryl, alkylaryl, heteroalkyl or heteroalkylaryl group containing up to 30 carbon atoms, wherein the heteroalkyl group contains from 1 to 10 heteroatoms independently selected from O, $NR^3$ and S and the heteroalkylaryl group contains from 1 to 3 heteroatoms independently selected from O, $NR^3$ and S; and
$A^1$ at each occurrence is independently selected from:
a bond,

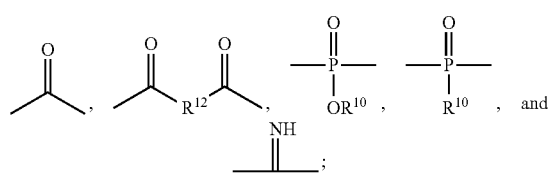

$R^{10}$ is selected from H, $C_1$-$C_{30}$ alkyl, alkenyl or alkynyl and $C_2$-$C_{30}$ heteroalkyl; heteroalkenyl or heteroalkynyl;
$R^{12}$ is selected from $C_1$-$C_{30}$ alkyl, alkenyl or alkynyl, $C_1$-$C_{30}$ heteroalkyl; heteroalkenyl or heteroalkynyl, $C_5$-$C_{30}$ heteroalkylaryl, heteroalkenylary or heteroalkynylaryl, $C_6$-$C_{30}$ alkylaryl, alkenylaryl or alkynylaryl, and $C_5$-$C_{30}$ heteroaryl;
wherein the —$X^1$ and —O— groups on the left phenyl ring, at each occurrence, are independently at o-, m-, or p-positions; and
a second repeating unit of Formula (IIa):

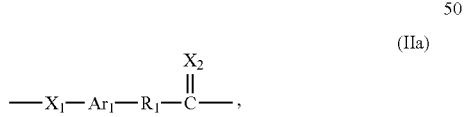

wherein:
$X_1$ and $X_2$ are independently selected from the group consisting of O, S and $NR_3$, wherein $R_3$ is selected from the group consisting of hydrogen and alkyl groups containing from one to 30 carbon atoms;
$Ar_1$ selected from the group consisting of phenyl,

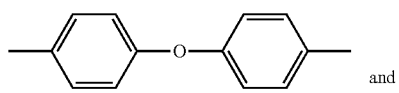

and

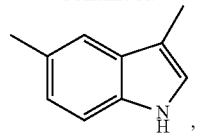

optionally substituted with from one to four substituents independently selected from the group consisting of halogen, halomethyl, halo-methoxy, methyl, methoxy, thiomethyl, nitro, sulfoxide and sulfonyl; and
$R_1$ is selected from the group consisting of an optionally substituted alkyl, heteroalkyl, alkenyl and heteroalkenyl groups containing from one to ten carbon atoms.
Heteroalkyl groups include oxyalkyl, aminoalkyl and thioalkyl. Heteroalkenyl groups include oxyalkenyl, aminoalkenyl and thioalkenyl.
In one embodiment of this aspect, the present invention provides a biocompatible polymer comprising a first repeating unit of Formula (Ia) and a second repeating unit of Formula (IIa), wherein $X_1$ and $X_2$ of Formula (IIa) are both oxygen atoms.
In another embodiment of this aspect, the present invention provides a biocompatible polymer comprising a first repeating unit of Formula (Ia) and a second repeating unit of Formula (IIa), wherein $Ar_1$ is a phenyl ring substituted with at least one halogen atom.
In another embodiment of this aspect, the present invention provides a biocompatible polymer comprising a first repeating unit of Formula (Ia) and a second repeating unit of Formula (IIa), wherein $Ar_1$ is a phenyl ring substituted with two iodine atoms in positions ortho to $X_1$.
In another embodiment of this aspect, the present invention provides a biocompatible polymer comprising a first repeating unit of Formula (Ia) and a second repeating unit of Formula (IIa), wherein $R_1$ is an oxyalkyl, aminoalkyl or thioalkyl group containing from one to ten carbon atoms.
In another embodiment of this aspect, the present invention provides a biocompatible polymer comprising a first repeating unit of Formula (Ia) and a second repeating unit of Formula (IIa), wherein $R_1$ is an oxyalkyl group containing two carbon atoms.
In another embodiment of this aspect, the present invention provides a biocompatible polymer comprising a first repeating unit of Formula (Ia) and a second repeating unit of Formula (IIa), wherein $A^1$ is a carbonyl having the structure:

In another embodiment of this aspect, the present invention provides a biocompatible polymer comprising a first repeating unit of Formula (Ia) and a second repeating unit of Formula (IIa), wherein i is 1, and the —O— group is at the o-position.
In another embodiment of this aspect, the present invention provides a biocompatible polymer comprising a first repeating unit of Formula (Ia) and a second repeating unit of Formula (IIa), wherein i is 1, and the —O— group is at the m-position.
In another embodiment of this aspect, the present invention provides a biocompatible polymer comprising a first repeating unit of Formula (Ia) and a second repeating unit of Formula (IIa), wherein i is 1, and the —O— group is at the p-position.

In another embodiment of this aspect, the present invention provides a biocompatible polymer comprising a first repeating unit of Formula (Ia) and a second repeating unit of Formula (IIa), wherein $R^3$ is hydrogen or $C_{1-6}$ alkyl, and $R^6$ is H or $C_{1-18}$ alkyl.

In another embodiment of this aspect, the present invention provides a biocompatible polymer comprising a first repeating unit of Formula (Ia) and a second repeating unit of Formula (IIa), wherein $R^3$ is hydrogen or $C_{1-6}$ alkyl, $R^6$ is H or $C_{1-18}$ alkyl, and the —O— group on the left phenyl ring is at the p-position.

In another embodiment of this aspect, the present invention provides a biocompatible polymer comprising a first repeating unit of Formula (Ia) and a second repeating unit of Formula (IIa), wherein $R^3$ is hydrogen or $C_{1-6}$ alkyl, $R^6$ is H or $C_{1-18}$ alkyl, and the —O— group on the left phenyl ring is at the p-position, and $A^1$ is carbonyl —C(=O)—.

The biocompatible polymers of the present invention in this aspect can be prepared by coupling of the monomer compounds of Formula (I) with the monomer compounds of Formula (II) using the synthetic Schemes (1) and (2) as follows (for illustration only, detailed conditions omitted):

While not limited thereto, in accordance with the above, a ring of $Ar_1$ may be substituted with two halogen atoms (e.g. iodine or bromine), preferably, in positions ortho to $X_1$.

In another aspect the present invention provides a biocompatible polymer comprising:

a first repeating unit of Formula (Ia):

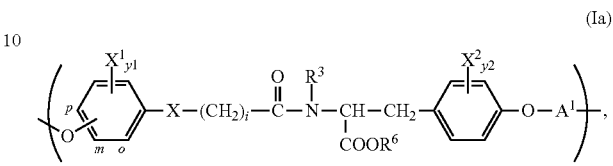

wherein:
i is an integer selected from 1 through 4;
$y^1$ and $y^2$ are each independently selected from 0, 1, 2, 3 and 4;
$X^1$ and $X^2$, at each occurrence, are independently bromine (Br) or iodine (I);
X is oxygen (O), sulfur (S), or $NR^4$; where $R^4$ is selected from the group consisting of hydrogen and alkyl containing from 1 to 6 carbon atoms Scheme 1

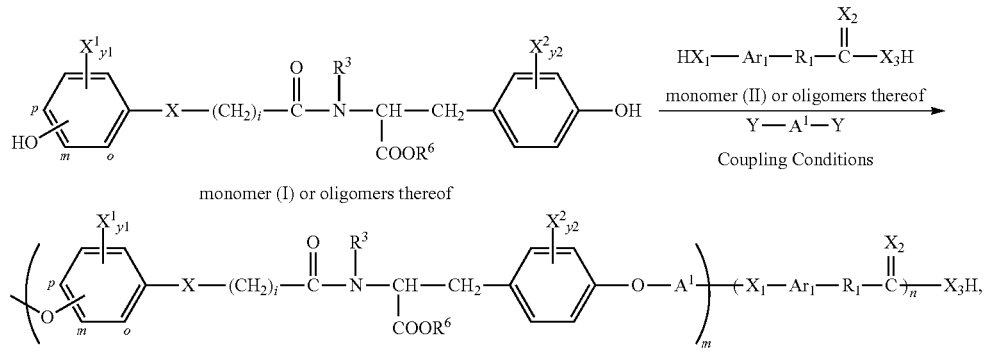

$R^3$ is an optionally substituted $C_{1-30}$ alkyl;

Scheme 2

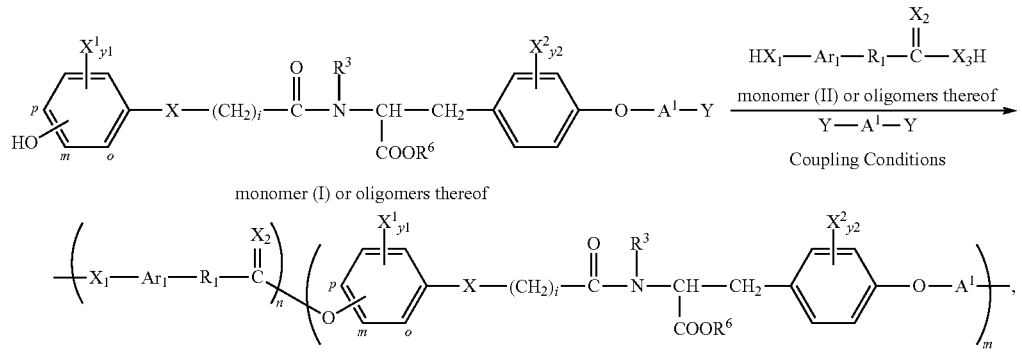

wherein $A^1$ is defined above, and Y is, for example, a halogen. The detailed conditions are provided in the Examples, or otherwise within the grasp of a person of ordinary skill in the art by following the disclosures herein.

$R^6$ is hydrogen or an alkyl, aryl, alkylaryl, heteroalkyl or heteroalkylaryl group containing up to 30 carbon atoms, wherein the heteroalkyl group contains from 1 to 10 heteroatoms independently selected from O, $NR^3$ and S and the heteroalkylaryl group contains from 1 to 3 heteroatoms independently selected from O, $NR^3$ and S; and $A^1$ at each occurrence is independently selected from:
a bond,

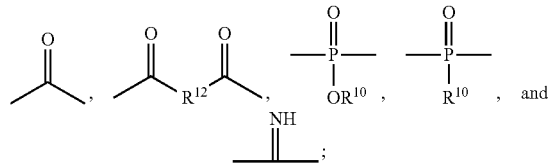

$R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkyl, alkenyl or alkynyl, $C_1$-$C_{30}$ heteroalkyl; heteroalkenyl or heteroalkynyl, $C_5$-$C_{30}$ heteroalkylaryl, heteroalkenylary or heteroalkynylaryl, $C_6$-$C_{30}$ alkylaryl, alkenylaryl or alkynylaryl, and $C_5$-$C_{30}$ heteroaryl;

wherein the —$X^1$ and —O— groups on the left phenyl ring, at each occurrence, are independently at o-, m-, or p-positions; and a second repeating unit of Formula (IIIa):

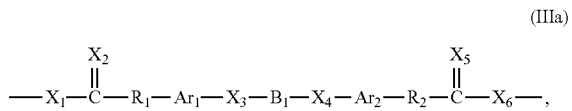

wherein:

$X_1$, $X_2$, $X_3$, $X_4$, $X_5$, and $X_6$ are independently selected from the group consisting of O, S and $NR_3$ wherein $R_3$ is selected from the group consisting of hydrogen and alkyl groups containing from 1 to 30 carbon atoms;

$Ar_1$ and $Ar_2$ are independently selected from the group consisting of phenyl,

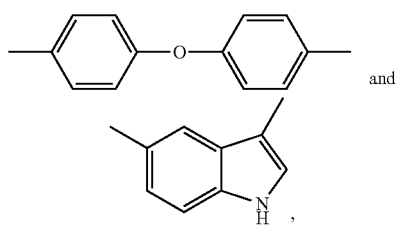

optionally substituted with from one to four substituents independently selected from the group consisting of halogen, halomethyl, halomethoxy, methyl, methoxy, thiomethyl, nitro, sulfoxide, and sulfonyl;

$R_1$ and $R_2$ are independently selected from the group consisting of an optionally substituted alkyl, heteroalkyl, alkenyl and heteroalkenyl groups containing from one to ten carbon atoms; and $B_1$ is a carbonyl group.

In one embodiment of this aspect, the present invention provides a biocompatible polymer comprising a first repeating unit of Formula (Ia) and a second repeating unit of Formula (IIIa), wherein each of $X_1$, $X_2$, $X_3$, $X_4$, $X_5$, and $X_6$ is an oxygen atom.

In another embodiment of this aspect, the present invention provides a biocompatible polymer comprising a first repeating unit of Formula (Ia) and a second repeating unit of Formula (IIIa), wherein $Ar_1$ and $Ar_2$ are each independently a phenyl ring substituted with at least one halogen atom.

In another embodiment of this aspect, the present invention provides a biocompatible polymer comprising a first repeating unit of Formula (Ia) and a second repeating unit of Formula (IIIa), wherein $Ar_1$ and $Ar_2$ are both a phenyl ring substituted with two iodine atoms.

In another embodiment of this aspect, the present invention provides a biocompatible polymer comprising a first repeating unit of Formula (Ia) and a second repeating unit of Formula (IIIa), wherein $R_1$ and $R_2$ are each independently oxyalkylene groups containing from one to ten carbon atoms.

In another embodiment of this aspect, the present invention provides a biocompatible polymer comprising a first repeating unit of Formula (Ia) and a second repeating unit of Formula (IIIa), wherein $R_1$ and $R_2$ are both oxymethylene groups.

In another embodiment of this aspect, the present invention provides a biocompatible polymer comprising a first repeating unit of Formula (Ia) and a second repeating unit of Formula (IIIa), characterized in that said polymer is a block copolymer with a hydroxy endcapped macromer, a mercapto endcapped macromer or an amino endcapped macromer.

In another embodiment of this aspect, the present invention provides a biocompatible polymer comprising a first repeating unit of Formula (Ia) and a second repeating unit of Formula (IIIa), characterized in that said polymer is a block copolymer with a hydroxy endcapped macromer, a mercapto endcapped macromer or an amino endcapped macromer, wherein said hydroxy endcapped macromer block comprises at least one macromer block selected from the group consisting of a hydroxy endcapped poly-caprolactone, a hydroxy endcapped polylactic acid, a hydroxy endcapped polyglycolic acid, a hydroxy endcapped poly(lactic acid-co-glycolic acid), a hydroxy endcapped poly(alkylene diol), a poly(alkylene oxide) and a hydroxy endcapped polydioxanone.

In another embodiment of this aspect, the present invention provides a biocompatible polymer comprising a first repeating unit of Formula (Ia) and a second repeating unit of Formula (IIIa), characterized in that said polymer is a block copolymer with a hydroxy endcapped macromer, a mercapto endcapped macromer or an amino endcapped macromer, as described above, wherein said alkylene diol is hexane diol.

In another embodiment of this aspect, the present invention provides a biocompatible polymer comprising a first repeating unit of Formula (Ia) and a second repeating unit of Formula (IIIa), characterized in that said polymer is a block copolymer with a hydroxy endcapped macromer, a mercapto endcapped macromer or an amino endcapped macromer, as described above, wherein the weight ratio of said polymer to said hydroxy-capped macromer is between about 25:75 and about 99:1.

In another embodiment of this aspect, the present invention provides a biocompatible polymer comprising a first repeating unit of Formula (Ia) and a second repeating unit of Formula (IIIa), comprising at least one repeating unit having the structure (IIIb):

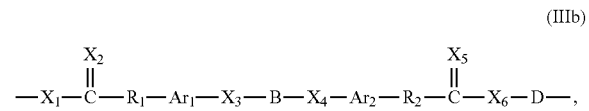

wherein $HX_6$-D-$X_1$H defines an alkylene diol containing up to 24 carbon atoms, an alkylene diamine containing up to 24 carbon atoms, an alkylene dimercaptan containing up to 24 carbon atoms, a hydroxy endcapped macromer, a mercapto endcapped macromer or an amine endcapped macromer.

The monomer compounds comprising Formula (IIIb) are disclosed in PCT Publication No. WO 2010/042918, which is incorporated by reference in its entirety.

In another embodiment of this aspect, the present invention provides a biocompatible polymer comprising a first repeating unit of Formula (Ia), a second repeating unit of Formula (IIIa), and a third repeating unit of Formula (IIIb), wherein said hydroxy endcapped macromer block comprises at least one macromer block selected from the group consisting of a hydroxy endcapped poly-caprolactone, a hydroxy endcapped polylactic acid, a hydroxy endcapped polyglycolic acid, a hydroxy endcapped poly(lactic acid-co-glycolic acid), a hydroxy endcapped poly(alkylene diol), a poly(alkylene oxide) and a hydroxy endcapped polydioxanone.

In another embodiment of this aspect, the present invention provides a biocompatible polymer comprising a first repeating unit of Formula (Ia) and a second repeating unit of Formula (IIIa), wherein the —O— group on the left phenyl ring of Formula (Ia) is at an o-position.

In another embodiment of this aspect, the present invention provides a biocompatible polymer comprising a first repeating unit of Formula (Ia) and a second repeating unit of Formula (IIIa), wherein the —O— group on the left phenyl ring of Formula (Ia) is at an m-position.

In another embodiment of this aspect, the present invention provides a biocompatible polymer comprising a first repeating unit of Formula (Ia) and a second repeating unit of Formula (IIIa), wherein the —O— group on the left phenyl ring of Formula (Ia) is at an p-position.

In another embodiment of this aspect, the present invention provides a biocompatible polymer comprising a first repeating unit of Formula (Ia) and a second repeating unit of Formula (IIIa), wherein i is 1

In another embodiment of this aspect, the present invention provides a biocompatible polymer comprising a first repeating unit of Formula (Ia) and a second repeating unit of Formula (IIIa), wherein $R^3$ is hydrogen or $C_{1-6}$ alkyl, and $R^6$ is H or $C_{1-18}$ alkyl.

In another embodiment of this aspect, the present invention provides a biocompatible polymer comprising a first repeating unit of Formula (Ia) and a second repeating unit of Formula (IIIa), wherein $R^3$ is hydrogen or $C_{1-6}$ alkyl, $R^6$ is H or $C_{1-18}$ alkyl, and the —O— group on the left phenyl ring is at the p-position.

In another embodiment of this aspect, the present invention provides a biocompatible polymer comprising a first repeating unit of Formula (Ia) and a second repeating unit of Formula (IIIa) where $R^3$ is hydrogen or $C_{1-6}$ alkyl, $R^6$ is H or $C_{1-18}$ alkyl, and the —O— group on the left phenyl ring is at the p-position, and $A^1$ is carbonyl —C(=O)—.

In another aspect the present invention provides a biocompatible polymer comprising:
a first repeating unit of Formula (Ia):

(Ia)

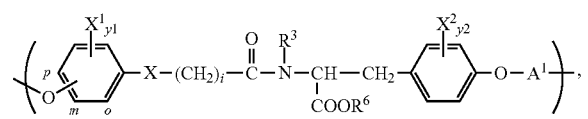

wherein:
i is an integer selected from 1 through 4;
$y^1$ and $y^2$ are each independently selected from 0, 1, 2, 3 and 4;
$X^1$ and $X^2$, at each occurrence, are independently bromine (Br) or iodine (I);

X is oxygen (O), sulfur (S), or $NR^4$; where $R^4$ is selected from the group consisting of hydrogen and alkyl containing from 1 to 6 carbon atoms $R^3$ is an optionally substituted $C_{1-30}$ alkyl; and $R^6$ is hydrogen or an alkyl, aryl, alkylaryl, heteroalkyl or heteroalkylaryl group containing up to 30 carbon atoms, wherein the heteroalkyl group contains from 1 to 10 heteroatoms independently selected from O, $NR^3$ and S and the heteroalkylaryl group contains from 1 to 3 heteroatoms independently selected from O, $NR^3$ and S;

wherein the —$X^1$ and —O— groups on the left phenyl ring, at each occurrence, are independently at o-, m-, or p-positions; and a second repeating unit of Formula (IVa):

(IVa)

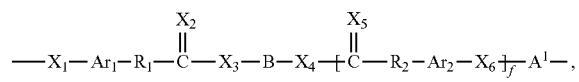

wherein:
f is 0 or 1;

$X_1, X_2, X_3, X_4, X_5,$ and $X_6$ are independently selected from the group consisting of O, S and $NR_3$ wherein $R_3$ is selected from the group consisting of hydrogen and alkyl groups containing from 1 to 30 carbon atoms;

$Ar_1$ and $Ar_2$ are independently selected from the group consisting of phenyl,

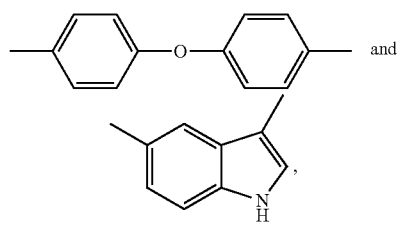

optionally substituted with from one to four substituents independently selected from the group consisting of halogen, halo-methyl, halomethoxy, methyl, methoxy, thiomethyl, nitro, sulfoxide, and sulfonyl;

R1 and R2 are independently selected from the group consisting of an optionally substituted alkyl, heteroalkyl, alkenyl and heteroalkenyl groups containing from one to ten carbon atoms;

B is selected from the group consisting of a carbonyl group and a group having the structure:

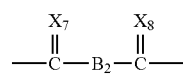

wherein $B_2$ is selected from the group consisting of an optionally substituted alkyl group, an optionally substituted heteroalkyl group, an optionally substituted alkenyl group and an optionally substituted heteroalkenyl group, or $B_2, X_3,$ $X_4, X_7$ and $X_8$ are selected so that

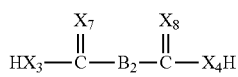

defines a capped macromer structure; and
$A^1$ at each occurrence is independently selected from:
a bond,

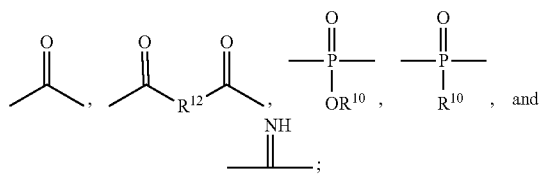

$R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkyl, alkenyl or alkynyl, $C_1$-$C_{30}$ heteroalkyl; heteroalkenyl or heteroalkynyl, $C_5$-$C_{30}$ heteroalkylaryl, heteroalkenylary or heteroalkynylaryl, $C_6$-$C_{30}$ alkylaryl, alkenylaryl or alkynylaryl, and $C_5$-$C_{30}$ heteroaryl.

In one embodiment of this aspect, the present invention provides a biocompatible polymer comprising a first repeating unit of Formula (Ia) and a second repeating unit of Formula (IVa), wherein said capped macromer structure is an macromer dicarboxylate.

In another embodiment of this aspect, the present invention provides a biocompatible polymer comprising a first repeating unit of Formula (Ia) and a second repeating unit of Formula (IVa), wherein each $X_1$, $X_2$, $X_3$, $X_4$, $X_5$, and $X_6$ is an O atom.

In another embodiment of this aspect, the present invention provides a biocompatible polymer comprising a first repeating unit of Formula (Ia) and a second repeating unit of Formula (IVa), wherein each of $Ar_1$ and $Ar_2$ is independently a phenyl ring substituted with at least one halogen atom.

In another embodiment of this aspect, the present invention provides a biocompatible polymer comprising a first repeating unit of Formula (Ia) and a second repeating unit of Formula (IVa), wherein $Ar_1$ and $Ar_2$ are both phenyl rings substituted with two iodine atoms.

In another embodiment of this aspect, the present invention provides a biocompatible polymer comprising a first repeating unit of Formula (Ia) and a second repeating unit of Formula (IVa), wherein $R_1$ and $R_2$ are each independently an oxyalkyl group containing from one to ten carbon atoms.

In another embodiment of this aspect, the present invention provides a biocompatible polymer comprising a first repeating unit of Formula (Ia) and a second repeating unit of Formula (IVa), wherein $R_1$ and $R_2$ are both oxymethyls.

In another embodiment of this aspect, the present invention provides a biocompatible polymer comprising a first repeating unit of Formula (Ia) and a second repeating unit of Formula (IVa), wherein $B_2$ is an alkyl group containing up to 18 carbon atoms.

In another embodiment of this aspect, the present invention provides a biocompatible polymer comprising a first repeating unit of Formula (Ia) and a second repeating unit of Formula (IVa), wherein $B_2$ is an alkyl group containing any number of carbon atoms selected from the group consisting of three carbon atoms, five carbon atoms and six carbon atoms.

In another embodiment of this aspect, the present invention provides a biocompatible polymer comprising a first repeating unit of Formula (Ia) and a second repeating unit of Formula (IVa), wherein said macromer dicarboxylate comprises a polylactic acid macromer block.

In another embodiment of this aspect, the present invention provides a biocompatible polymer comprising a first repeating unit of Formula (Ia) and a second repeating unit of Formula (IVa), wherein said macromer dicarboxylate comprises a polyglycolic acid macromer block.

In another embodiment of this aspect, the present invention provides a biocompatible polymer comprising a first repeating unit of Formula (Ia) and a second repeating unit of Formula (IVa), wherein said macromer dicarboxylate comprises a poly(lactic acid-co-glycolic acid) macromer block.

In another embodiment of this aspect, the present invention provides a biocompatible polymer comprising a first repeating unit of Formula (Ia) and a second repeating unit of Formula (IVa), wherein said macromer dicarboxylate comprises a polycaprolactone macromer block.

In another embodiment of this aspect, the present invention provides a biocompatible polymer comprising a first repeating unit of Formula (Ia) and a second repeating unit of Formula (IVa), wherein said macromer dicarboxylate comprises at least one macromer block selected from the group consisting of a hydroxy end-capped polyalkylene diol, a polyalkylene oxide and a hydroxy endcapped polydioxanone.

In another embodiment of this aspect, the present invention provides a biocompatible polymer comprising a first repeating unit of Formula (Ia) and a second repeating unit of Formula (IVa) described above, wherein the alkylene diol is hexane diol.

In another embodiment of this aspect, the present invention provides a biocompatible polymer comprising a first repeating unit of Formula (Ia) and a second repeating unit of Formula (IVa), characterized in that said polymer is a block copolymer with a hydroxy endcapped macromer, a mercapto endcapped macromer or an amine endcapped macromer.

In another embodiment of this aspect, the present invention provides a biocompatible polymer comprising a first repeating unit of Formula (Ia) and a second repeating unit of Formula (IVa), as described above, wherein said hydroxy endcapped macromer block comprises at least one macromer block selected from the group consisting of a hydroxy endcapped polycaprolactone, a hydroxy endcapped polylactic acid, a hydroxy endcapped polyglycolic acid, a hydroxy endcapped poly(lactic acid-co-glycolic acid), a hydroxy endcapped poly(alkylene diol), a poly(alkylene oxide) and a hydroxy endcapped polydioxanone.

In another embodiment of this aspect, the present invention provides a biocompatible polymer comprising a first repeating unit of Formula (Ia) and a second repeating unit of Formula (IVa), described above, wherein the alkylene diol is hexane diol.

In another embodiment of this aspect, the present invention provides a biocompatible polymer comprising a first repeating unit of Formula (Ia) and a second repeating unit of Formula (IVa), as described above, wherein the weight ratio of said polymer to said hydroxy-capped macromer is between about 25:75 and about 99:1.

In another embodiment of this aspect, the present invention provides a biocompatible polymer comprising a first repeating unit of Formula (Ia) and a second repeating unit of Formula (IVa), wherein $A^1$ is a carbonyl group having the following structure:

In another embodiment of this aspect, the present invention provides a biocompatible polymer comprising a first repeating unit of Formula (Ia) and a second repeating unit of Formula (IVa), wherein $A^1$ is group having the structure:

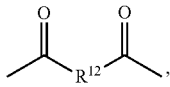

wherein $R^{12}$ is selected from the group consisting of alkyl, heteroalkyl, alkenyl and heteroalkenyl groups containing from one to 18 carbon atoms.

In another embodiment of this aspect, the present invention provides a biocompatible polymer comprising a first repeating unit of Formula (Ia) and a second repeating unit of Formula (IVa), wherein the —O— group on the left phenyl ring of Formula (Ia) is at an o-position.

In another embodiment of this aspect, the present invention provides a biocompatible polymer comprising a first repeating unit of Formula (Ia) and a second repeating unit of Formula (IVa), wherein the —O— group on the left phenyl ring of Formula (Ia) is at an m-position.

In another embodiment of this aspect, the present invention provides a biocompatible polymer comprising a first repeating unit of Formula (Ia) and a second repeating unit of Formula (IVa), wherein the —O— group on the left phenyl ring of Formula (Ia) is at an p-position.

In another embodiment of this aspect, the present invention provides a biocompatible polymer comprising a first repeating unit of Formula (Ia) and a second repeating unit of Formula (IVa), wherein i is 1

In another embodiment of this aspect, the present invention provides a biocompatible polymer comprising a first repeating unit of Formula (Ia) and a second repeating unit of Formula (IVa), wherein $R^3$ is hydrogen or $C_{1-6}$ alkyl, and $R^6$ is H or $C_{1-18}$ alkyl.

In another embodiment of this aspect, the present invention provides a biocompatible polymer comprising a first repeating unit of Formula (Ia) and a second repeating unit of Formula (IVa), wherein $R^3$ is hydrogen or $C_{1-6}$ alkyl, $R^6$ is H or $C_{1-18}$ alkyl, and the —O— group on the left phenyl ring is at the p-position.

In another embodiment of this aspect the present invention provides a biocompatible polymer comprising a first repeating unit of Formula (Ia) and a second repeating unit of Formula (IVa), wherein $R^3$ is hydrogen or $C_{1-6}$ alkyl, $R^6$ is H or $C_{1-18}$ alkyl, and the —O— group on the left phenyl ring is at the p-position, and $A^1$ is carbonyl —C(=O)—.

An embodiment is provided in which the "X" groups and $R_1$ are selected so that the monomers and polymers are derivatives of hydroxy-aryloxyalkanoic, hydroxy-arylaminoalkanoic, hydroxy-arylthioalkanoic, hydroxy-aryloxyalkenoic, hydroxy-arylaminoalkenoic and hydroxy-arylthioalkenoic acids wherein the aryl group is a phenyl, phenoxyphenyl or indole ring. Examples of such acids include 4-hydroxycinnamic acid, 4-hydroxybenzoic acid, 2-(4-hydroxyphenoxy) ethanoic acid, 3-(4-hydroxyphenoxy)propanoic acid, 4-(4-hydroxyphenoxy)butanoic acid, 5-hydroxy-1H-indol-3-yl-carboxylic acid, 2-(5-hydroxy-1H-indol-3-yl)ethanoic acid, 3-(5-hydroxy-1H-indol-3-yl)propanoic acid (5-hydroxy-desamino-tryptophan), 4-(5-hydroxy-1H-indol-3-yl)butanoic acid, 4-hydroxy-phenoxybenzoic acid, 2-(4-hydroxy-phenoxy-phenoxy)ethanoic acid, 3-(4-hydroxyphenoxy-phenoxy)propanoic acid, 4-(4-hydroxy-phenoxy-phenoxy)butanoic acid, and the like. Hydroxy-arylalkenoic acid and hydroxy-arylalkenoic acids from which monomers and polymers may be derived have the structure of Formula (II), and compounds in which the "X" groups are all oxygens have the structure:

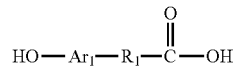

wherein $Ar_1$ and $R_1$ and the preferred species thereof are the same as described above with respect to Formula (II).

Based on the foregoing, in certain embodiments of the biocompatible polymers, $A^1$ is a carbonyl group having the following structure:

wherein the carbonyl group is derived from a phosgene starting material. This method is essentially the conventional method for polymerizing diols into polycarbonates. Suitable processes, associated catalysts and solvents are known in the art and are taught in Schnell, Chemistry and Physics of Polycarbonates, (Interscience, New York 1964), the teachings of which are incorporated herein by reference. Because $X_1$ and $X_6$ are independently selected from O, S and $NR_3$, the reaction of formula II monomers with phosgene may also produce urethane linkages (—$NR_3$—(C=O)—$NR_3$—), carbonodithioate linkages (—S—(C=O)—S—), carbamate linkages (—O—(C=O)—$NR_3$—), thiocarbonate linkages (—S—(C=O)—O—) and thiocarbamate linkages (—S—(C=O)—$NR_3$—). Other methods adaptable for use to prepare the polycarbonate and other phosgene-derived polymers of the present invention are disclosed in U.S. Pat. Nos. 6,120,491 and 6,475,477 the disclosures of which are incorporated by reference.

In another embodiment, $A^1$ is a group having the structure:

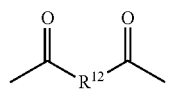

which is derived from a carboxylic acid starting material. When the monomer of Formula IIa is a diphenol, the Formula IIc polymer is formed by reaction of the diphenol with an aliphatic or aromatic dicarboxylic acids in the carbodiimide mediated process disclosed by U.S. Pat. No. 5,216,115 using 4-(dimethylamino) pyridinium-p-toluene sulfonate (DPTS) as a catalyst. The disclosure of U.S. Pat. No. 5,216,115 is incorporated by reference.

The foregoing process forms polymers with —O—C(=O)—$R_{12}$—C(=O)—O— linkages. $R_{12}$ may be selected so that the dicarboxylic acids employed as starting materials are either important naturally-occurring metabolites or highly biocompatible compounds. Aliphatic dicarboxylic acid starting materials therefore include the intermediate dicarboxylic acids of the cellular respiration pathway known as the Krebs Cycle. The dicarboxylic acids include α-ketoglutaric acid, succinic acid, fumaric acid and oxaloacetic acid ($R_{12}$ may be —$CH_2$—$CH_2$—C(=O)—, —$CH_2$—$CH_2$—, —CH=CH— and —$CH_2$—C(=O)—, respectively).

Yet another naturally occurring aliphatic dicarboxylic acid is adipic acid ($R_{12}$ is (—$CH_2$—)$_4$), found in beet juice. Still another biocompatible aliphatic dicarboxylic acid is sebacic acid ($R_{12}$ is (—$CH_2$—)$_8$), which has been studied extensively and has been found to be nontoxic as part of the clinical evaluation of poly(bis(p-carboxyphenoxy)propane-co-sebacic acid anhydride) by Laurencin et al., J. Biomed. Mater. Res., 24, 1463-81 (1990).

Other biocompatible aliphatic dicarboxylic acids include oxalic acid ($R_{12}$ is a bond), malonic acid ($R_{12}$ is —$CH_2$—), glutaric acid ($R_{12}$ is (—$CH_2$—)$_3$), pimelic acid ($R_{12}$ is (—$CH_2$—)$_5$), suberic acid ($R_{12}$ is (—$CH_2$—)$_6$) and azelaic acid ($R_{12}$ is (—$CH_2$—)$_7$). $R_{12}$ can thus represent (—$CH_2$—)$_Q$, where Q is between 0 and 8, inclusive. Among the suitable aromatic dicarboxylic acids are terephthalic acid, isophthalic acid and bis(p-carboxy-phenoxy)alkanes such as bis(p-carboxy-phenoxy) propane.

$R_{12}$ can also have the structure:

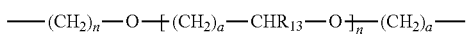

wherein a is 1, 2 or 3, inclusive, m is from 1 to 500,000, inclusive, and $R_{13}$ is hydrogen or a lower alkyl group containing from one to four carbon atoms. $R_{13}$ is preferably hydrogen, a is preferably 1, and m is preferably between about 10 and about 100, and more preferably between about 10 and about 50.

$R_{12}$ can also have the structure:

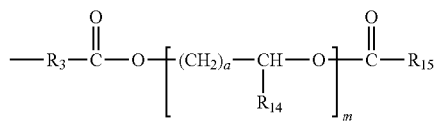

wherein a, m and $R_{14}$ and the preferred species thereof are the same as described above. $R_{15}$ is selected from a bond or straight and branched alkyl and alkylaryl groups containing up to 18 carbon atoms.

Polymers of the present invention include block copolymers with a hydroxy endcapped macromer, a mercapto endcapped macromer or an amino endcapped macromer. For example, a hydroxy endcapped macromer can be added to the reaction between a diphenol and phosgene to form a polycarbonate macromer block copolymer, or it can be added to the reaction between a diphenol and a dicarboxylic acid to form a polyarylate macromer block copolymer.

Molar fractions of macromer units range from greater than zero to less than one and are typically greater than zero up to about 0.5. Embodiments include an macromer molar fraction between about 0.10 and about 0.25.

It is difficult to prepare polymers with pendent free carboxylic acid groups by polymerization of corresponding monomers with pendent free carboxylic acid groups without cross-reaction of the free carboxylic acid group with the co-monomer. Accordingly, polymers having pendent free carboxylic acid groups are preferably prepared from the corresponding benzyl and tert-butyl ester polymers ($R_4$ is a benzyl or t-butyl group).

The benzyl ester polymers may be converted to the corresponding free carboxylic acid polymers through the selective removal of the benzyl groups by the palladium catalyzed hydrogenolysis method disclosed in U.S. Pat. No. 6,120,491, the disclosure of which is incorporated herein by reference, and particularly for the purpose of describing such methods. The tert-butyl ester polymers may be converted to the corresponding free carboxylic acid polymers through the selective removal of the tert-butyl groups by the acidolyis method disclosed in U.S. Patent Publication No. 20060034769, also incorporated herein by reference, and particularly for the purpose of describing such methods. The catalytic hydrogenolysis or acidolysis is preferable because the lability of the polymer backbone tends to discourage the employment of harsher hydrolysis techniques.

The molar fraction of free carboxylic acid units in the polymers described herein can be adjusted to modify the degradation of devices made from such polymers. For example, polymers with lower amounts of free carboxylic acid will tend to have longer lifetimes in the body. Further, by otherwise adjusting the amount of free carboxylic acid in the polymers across the range of preferred molar fraction, the resulting polymers can be adapted for use in various applications requiring different device lifetimes. In general, the higher the molar fraction of free carboxylic acid units, the shorter the lifetime of the device in the body and more suitable such devices are for applications wherein shorter lifetimes are desirable or required.

Polymers with a sufficient number of aromatic rings that are sufficiently substituted with bromine or iodine are inherently radiopaque. Various aromatic rings in both the first polymer phase and the second polymer phase can be iodine or bromine substituted. For example, independent of any particular polymer embodiment, the aromatic rings of the recurring units of the Formula (Ia), (IIa), (IIIa), or (IVa) may be substituted with at least one iodine or bromine atom, on at least one and preferably on both ring positions. In an embodiment, at least 50% of the aromatic rings of recurring units of the formula (Ia), (IIa), (IIIa), or (IVa) in a polymer composition are substituted with from two to four iodine or bromine atoms.

The radiopaque monomers may be prepared according to the disclosure of U.S. Pat. No. 6,475,477, or the disclosure of U.S. Patent Publication No. 2006/0034769, the disclosures of both of which are incorporated herein by reference, and particularly for the purpose of describing such monomers and methods of making them. The iodinated and brominated phenolic monomers described herein can also be employed as radiopacifying, biocompatible non-toxic additives for biocompatible polymer compositions, as provided herein. Iodinated and brominated polymers may be polymerized from iodinate and brominated monomers, or the polymers can be iodinated or brominated after polymerization.

In another radiopaque polymer embodiment, methylene hydrogens are replaced with bromine or iodine to increase polymer radio-opacity. Such substitution may be concurrent with or in place of halogen substituted phenyl groups, as discussed above. Accordingly, radio-opaque polylactic acids, polyglycolic acids and polylactic-co-glycolic acids are provided by replacing a sufficient number of methylene hydrogens with bromine, iodine or both. A preferred radio-opaque polylactic acid contains lactic acid units with pendant tri-iodomethyl groups.

After polymerization of any of the foregoing compounds or monomers, appropriate work up of the polymers in accordance with preferred embodiments of the present invention may be achieved by any of a variety of known methods commonly employed in the field of synthetic polymers to produce a variety of useful articles with valuable physical and chemical properties.

Medical Uses

Various embodiments of the polymer compositions described herein, preferably derived from tissue compatible monomers, may be used to produce a variety of useful articles with valuable physical and chemical properties. The useful articles can be shaped by conventional polymer thermo-forming techniques such as extrusion and injection molding when the degradation temperature of the polymer is above the glass transition or crystalline melt temperature(s), or conventional non-thermal techniques can be used, such as compression molding, injection molding, solvent casting, spin casting, wet spinning. Combinations of two or more methods can be used. Shaped articles prepared from the polymers are useful, inter alia, as biocompatible, biodegradable and/or bioresorbable biomaterials for medical implant applications.

In one embodiment, the medical device is a stent. It is contemplated that a stent may comprise many different types of forms. For instance, the stent may be an expandable stent. In another embodiment, the stent may be configured to have the form of a sheet stent, a braided stent, a self-expanding stent, a woven stent, a deformable stent, or a slide-and-lock stent. Stent fabrication processes may further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms.

In certain other embodiments, the polymers are formed into coatings on the surface of an implantable device, particularly a stent, made either of a polymer of the present invention or another material, such as metal. Such coatings may be formed on stents via techniques such as dipping, spray coating, combinations thereof, and the like. Further, stents may be comprised of at least one fiber material, curable material, laminated material, and/or woven material. The medical device may also be a stent graft or a device used in embolotherapy.

Details of stent products and fabrication in which the polymers disclosed herein may be employed are disclosed in US Pat. Publication No. 2006/0034769, the disclosure of which is incorporated by reference. Stents are preferably fabricated from the radiopaque polymers of the present invention, to permit fluoroscopic positioning of the device.

The highly beneficial combination of properties associated with the polymers disclosed herein means these polymers are well-suited for use in producing a variety of resorbable medical devices besides stents, especially implantable medical devices that are preferably radiopaque, biocompatible, and have various times of bioresorption. For example the polymers are suitable for use in resorbable implantable devices with and without therapeutic agents, device components and/or coatings with and without therapeutic agents for use in other medical systems, for instance, the musculoskeletal or orthopedic system (e.g., tendons, ligaments, bone, cartilage skeletal, smooth muscles); the nervous system (e.g., spinal cord, brain, eyes, inner ear); the respiratory system (e.g., nasal cavity and sinuses, trachea, larynx, lungs); the reproductive system (e.g., male or female reproductive); the urinary system (e.g., kidneys, bladder, urethra, ureter); the digestive system (e.g., oral cavity, teeth, salivary glands, pharynx, esophagus, stomach, small intestine, colon), exocrine functions (biliary tract, gall bladder, liver, appendix, recto-anal canal); the endocrine system (e.g., pancreas/islets, pituitary, parathyroid, thyroid, adrenal and pineal body), the hematopoietic system (e.g., blood and bone marrow, lymph nodes, spleen, thymus, lymphatic vessels); and, the integumentary system (e.g., skin, hair, nails, sweat glands, sebaceous glands).

The polymers described herein can thus be used to fabricate wound closure devices, hernia repair meshes, gastric lap bands, drug delivery implants, envelopes for the implantation of cardiac devices, devices for other cardiovascular applications, non-cardiovascular stents such as biliary stents, esophageal stents, vaginal stents, lung-trachea/bronchus stents, and the like.

In addition, the resorbable polymers are suitable for use in producing implantable, radiopaque discs, plugs, and other devices used to track regions of tissue removal, for example, in the removal of cancerous tissue and organ removal, as well as, staples and clips suitable for use in wound closure, attaching tissue to bone and/or cartilage, stopping bleeding (homeostasis), tubal ligation, surgical adhesion prevention, and the like. Applicants have also recognized that the resorbable polymers disclosed herein are well-suited for use in producing a variety of coatings for medical devices, especially implantable medical devices.

In some embodiments, the disclosed polymers may be advantageously used in making various resorbable orthopedic devices including, for example, radiopaque biodegradable screws (interference screws), radiopaque biodegradable suture anchors, and the like for use in applications including the correction, prevention, reconstruction, and repair of the anterior cruciate ligament (ACL), the rotator cuff/rotator cup, and other skeletal deformities.

Other devices that can be advantageously formed from preferred embodiments of the polymers described herein include devices for use in tissue engineering. Examples of suitable resorbable devices include tissue engineering scaffolds and grafts (such as vascular grafts, grafts or implants used in nerve regeneration). The present resorbable polymers may also be used to form a variety of devices effective for use in closing internal wounds. For example biodegradable resorbable sutures, clips, staples, barbed or mesh sutures, implantable organ supports, and the like, for use in various surgery, cosmetic applications, and cardiac wound closures can be formed.

Various devices useful in dental applications may advantageously be formed from disclosed polymer embodiments. For example, devices for guided tissue regeneration, alveolar ridge replacement for denture wearers, and devices for the regeneration of maxilla-facial bones may benefit from being radiopaque so that the surgeon or dentist can ascertain the placement and continuous function of such implants by simple X-ray imaging.

Preferred embodiments of the polymers described herein are also useful in the production of bioresorbable, inherently radiopaque polymeric embolotherapy products for the temporary and therapeutic restriction or blocking of blood supply to treat tumors and vascular malformations, e.g., uterine fibroids, tumors (i.e., chemoembolization), hemorrhage (e.g., during trauma with bleeding) and arteriovenous malformations, fistulas and aneurysms delivered by means of catheter or syringe. Details of embolotherapy products and methods of fabrication in which polymer embodiments described herein may be employed are disclosed in U.S. Patent Publication No. 2005/0106119, the disclosure of which is incorporated by reference. Embolotherapy treatment methods are by their very nature local rather than systemic and the products are preferably fabricated from radiopaque polymers, such as the radiopaque polymers disclosed herein, to permit fluoroscopic monitoring of delivery and treatment.

The polymers described herein are further useful in the production of a wide variety of therapeutic agent delivery devices. Such devices may be adapted for use with a variety of therapeutics including, for example, pharmaceuticals (i.e., drugs) and/or biological agents as previously defined and including biomolecules, genetic material, and processed biologic materials, and the like. Any number of transport systems capable of delivering therapeutics to the body can be made, including devices for therapeutics delivery in the treatment of cancer, intravascular problems, dental problems, obesity, infection, and the like.

A medical device that comprises a polymeric material may include one or more additional components, e.g., a plasticizer, a filler, a crystallization nucleating agent, a preservative, a stabilizer, a photoactivation agent, etc., depending on the intended application. For example, in an embodiment, a medical device comprises an effective amount of at least one therapeutic agent and/or a magnetic resonance enhancing agent. Non-limiting examples of preferred therapeutic agents include a chemotherapeutic agent, a non-steroidal anti-inflammatory, a steroidal anti-inflammatory, and a wound healing agent. Therapeutic agents may be co-administered with the polymeric material. In a preferred embodiment, at least a portion of the therapeutic agent is contained within the polymeric material. In another embodiment, at least a portion of the therapeutic agent is contained within a coating on the surface of the medical device.

Non-limiting examples of preferred chemotherapeutic agents include taxanes, taxinines, taxols, paclitaxel, dioxorubicin, cis-platin, adriamycin, and bleomycin. Non-limiting examples of preferred non-steroidal anti-inflammatory compounds include aspirin, dexamethasone, ibuprofen, naproxen, and Cox-2 inhibitors (e.g., Rofexcoxib, Celecoxib and Valdecoxib). Non-limiting examples of preferred steroidal anti-inflammatory compounds include dexamethasone, beclomethasone, hydrocortisone, and prednisone. Mixtures comprising one or more therapeutic agents may be used. Non-limiting examples of preferred magnetic resonance enhancing agents include gadolinium salts such as gadolinium carbonate, gadolinium oxide, gadolinium chloride and mixtures thereof.

The amounts of additional components present in the medical device are preferably selected to be effective for the intended application. For example, a therapeutic agent is preferably present in the medical device in an amount that is effective to achieve the desired therapeutic effect in the patient to whom the medical device is administered or implanted. Such amounts may be determined by routine experimentation. In certain embodiments, the desired therapeutic effect is a biological response. In an embodiment, the therapeutic agent in the medical device is selected to promote at least one biological response, preferably a biological response selected from the group consisting of thrombosis, cell attachment, cell proliferation, attraction of inflammatory cells, deposition of matrix proteins, inhibition of thrombosis, inhibition of cell attachment, inhibition of cell proliferation, inhibition of inflammatory cells, and inhibition of deposition of matrix proteins. The amount of magnetic resonance enhancing agent in a medical devices is preferably an amount that is effective to facilitate radiologic imaging, and may be determined by routine experimentation.

The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" may include 1) "biomolecule", as used herein, encompassing a biologically active peptide, protein, carbohydrate, vitamin, lipid, or nucleic acid produced by and purified from naturally occurring or recombinant organisms, antibodies, tissues or cell lines or synthetic analogs of such molecules; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent may also include vitamin or mineral substances or other natural elements.

For devices placed in the vascular system, e.g., a stent, the amount of the therapeutic agent is preferably sufficient to inhibit restenosis or thrombosis or to affect some other state of the stented tissue, for instance, heal a vulnerable plaque, and/or prevent rupture or stimulate endothelialization. The agent(s) may be selected from the group consisting of anti-proliferative agents, anti-inflammatory, anti-matrix metalloproteinase, and lipid lowering, cholesterol modifying, anti-thrombotic and antiplatelet agents, in accordance with preferred embodiments of the present invention. In some preferred embodiments of the stent, the therapeutic agent is contained within the stent as the agent is blended with the polymer or admixed by other means known to those skilled in the art. In other preferred embodiments of the stent, the therapeutic agent is delivered from a polymer coating on the stent surface. In another preferred variation the therapeutic agent is delivered by means of no polymer coating. In other preferred embodiments of the stent, the therapeutic agent is delivered from at least one region or one surface of the stent. The therapeutic may be chemically bonded to the polymer or carrier used for delivery of the therapeutic of at least one portion of the stent and/or the therapeutic may be chemically bonded to the polymer that comprises at least one portion of the stent body. In one preferred embodiment, more than one therapeutic agent may be delivered.

In certain embodiments, any of the aforementioned devices described herein can be adapted for use as a therapeutic delivery device (in addition to any other functionality thereof). Controlled therapeutic delivery systems may be prepared, in which a therapeutic agent, such as a biologically or pharmaceutically active and/or passive agent, is physically embedded or dispersed within a polymeric matrix or physically admixed with a polymer described herein. Controlled therapeutic agent delivery systems may also be prepared by direct application of the therapeutic agent to the surface of an implantable medical device such as a bioresorbable stent device (comprised of at least one of the polymers described herein) without the use of these polymers as a coating, or by use of other polymers or substances for the coating.

In certain embodiments, any of the aforementioned devices described herein can be adapted for use as a therapeutic delivery device (in addition to any other functionality thereof). Controlled therapeutic delivery systems may be prepared, in which a therapeutic agent, such as a biologically or pharmaceutically active and/or passive agent, is physically embedded or dispersed within a polymeric matrix or physically admixed with a polymer embodiment. Controlled therapeutic agent delivery systems may also be prepared by direct application of the therapeutic agent to the surface of an implantable medical device such as a bioresorbable stent device (comprised of at least one of the present polymers) without the use of these polymers as a coating, or by use of other polymers or substances for the coating.

The therapeutic agent may first be covalently attached to a monomer, which is then polymerized, or the polymerization may be performed first, followed by covalent attachment of the therapeutic agent. Hydrolytically stable conjugates are utilized when the therapeutic agent is active in conjugated form. Hydrolyzable conjugates are utilized when the therapeutic agent is inactive in conjugated form.

Therapeutic agent delivery compounds may also be formed by physically blending the therapeutic agent to be delivered with the polymer embodiments using conventional techniques well-known to those of ordinary skill in the art. For this therapeutic agent delivery embodiment, it is not essential that the polymer have pendent groups for covalent attachment of the therapeutic agent.

The polymer compositions described herein containing therapeutic agents, regardless of whether they are in the form of polymer conjugates or physical admixtures of polymer and therapeutic agent, are suitable for applications where localized delivery is desired, as well as in situations where a systemic delivery is desired. The polymer conjugates and physical admixtures may be implanted in the body of a patient in need thereof, by procedures that are essentially conventional and well-known to those of ordinary skill in the art.

Implantable medical devices may thus be fabricated that also serve to deliver a therapeutic agent to the site of implantation by being fabricated from or coated with the therapeutic agent delivery system embodiment described herein in which a disclosed polymer embodiment has a therapeutic agent physically admixed therein or covalently bonded thereto, such as a drug-eluting stent. Covalent attachment requires a polymer to have a reactive pendant group. Embolotherapeutic particles may also be fabricated for delivery of a therapeutic agent.

Examples of biologically or pharmaceutically active therapeutic agents that may be physically admixed with or covalently attached to polymer embodiments disclosed herein include acyclovir, cephradine, malphalen, procaine, ephedrine, adriamycin, daunomycin, plumbagin, atropine, quinine, digoxin, quinidine, biologically active peptides, chlorin e.sub.6, cephradine, cephalothin, proline and proline analogs such as cis-hydroxy-L-proline, malphalen, penicillin V and other antibiotics, aspirin and other non-steroidal anti-inflammatory compounds, nicotinic acid, chemodeoxycholic acid, chlorambucil, anti-tumor and anti-proliferative agents, including anti-proliferative agents that prevent restenosis, hormones such as estrogen, and the like. Biologically active compounds, for purposes of the present invention, are additionally defined as including cell attachment mediators, biologically active ligands, and the like.

The invention described herein also includes various pharmaceutical dosage forms containing the polymer-therapeutic agent combinations described herein. The combination may be a bulk matrix for implantation or fine particles for administration by traditional means, in which case the dosage forms include those recognized conventionally, e.g. tablets, capsules, oral liquids and solutions, drops, parenteral solutions and suspensions, emulsions, oral powders, inhalable solutions or powders, aerosols, topical solutions, suspensions, emulsions, creams, lotions, ointments, transdermal liquids and the like.

The dosage forms may include one or more pharmaceutically acceptable carriers. Such materials are non-toxic to recipients at the dosages and concentrations employed, and include diluents, solubilizers, lubricants, suspending agents, encapsulating materials, penetration enhancers, solvents, emollients, thickeners, dispersants, buffers such as phosphate, citrate, acetate and other organic acid salts, anti-oxidants such as ascorbic acid, preservatives, low molecular weight (less than about 10 residues) peptides such as polyarginine, proteins such as serum albumin, gelatin, or immunoglobulins, other hydrophilic polymers such as poly(vinylpyrrolidinone), amino acids such as glycine, glutamic acid, aspartic acid, or arginine, monosaccharides, disaccharides, and other carbohydrates, including cellulose or its derivatives, glucose, mannose, or dextrines, chelating agents such as EDTA, sugar alcohols such as mannitol or sorbitol, counter-ions such as sodium and/or nonionic surfactants such as tween, pluronics or PEG.

Therapeutic agents to be incorporated in the polymer conjugates and physical admixture embodiments disclosed herein may be provided in a physiologically acceptable carrier, excipient stabilizer, etc., and may be provided in sustained release or timed release formulations supplemental to the polymeric formulation prepared in this invention. Liquid carriers and diluents for aqueous dispersions are also suitable for use with the polymer conjugates and physical admixtures.

Subjects in need of treatment, typically mammalian, using the disclosed polymer-therapeutic agent combinations, can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize. The polymer-therapeutic agent combinations may be prepared for storage under conditions suitable for the preservation of therapeutic agent activity as well as maintaining the integrity of the polymers, and are typically suitable for storage at ambient or refrigerated temperatures.

Depending upon the particular compound selected transdermal delivery may be an option, providing a relatively steady delivery of the drug, which is preferred in some circumstances. Transdermal delivery typically involves the use of a compound in solution with an alcoholic vehicle, optionally a penetration enhancer, such as a surfactant, and other optional ingredients. Matrix and reservoir type transdermal delivery systems are examples of suitable transdermal systems. Transdermal delivery differs from conventional topical treatment in that the dosage form delivers a systemic dose of the therapeutic agent to the patient.

The polymer-drug formulation described herein may also be administered in the form of liposome delivery systems, such as small unilamellar vesicles, large unilamellar vesicles and multilamellar vesicles. Liposomes may be used in any of the appropriate routes of administration described herein. For example, liposomes may be formulated that can be administered orally, parenterally, transdermally or via inhalation. Therapeutic agent toxicity could thus be reduced by selective delivery to the affected site. For example if the therapeutic agent is liposome encapsulated, and is injected intravenously, the liposomes used are taken up by vascular cells and locally high concentrations of the therapeutic agent could be released over time within the blood vessel wall, resulting in improved action of the therapeutic agent. The liposome encapsulated therapeutic agents are preferably administered parenterally, and particularly, by intravenous injection.

Liposomes may be targeted to a particular site for release of the therapeutic agent. This would obviate excessive dosages that are often necessary to provide a therapeutically useful dosage of a therapeutic agent at the site of activity, and consequently, the toxicity and side effects associated with higher dosages.

Therapeutic agents incorporated into the polymers of described herein may desirably further incorporate agents to facilitate their delivery systemically to the desired target, as long as the delivery agent meets the same eligibility criteria as the therapeutic agents described above. The active therapeutic agents to be delivered may in this fashion be incorporated with antibodies, antibody fragments, growth factors, hormones, or other targeting moieties, to which the therapeutic agent molecules are coupled.

The polymer-therapeutic agent combinations described herein may also be formed into shaped articles, such as valves, stents, tubing, prostheses, and the like. Cardiovascular stents may be combined with therapeutic agents that prevent restenosis. Implantable medical devices may be combined with therapeutic agents that prevent infection.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rates from the formulations of this invention are also varied within the routine skill in the art to determine an advantageous profile, depending on the therapeutic conditions to be treated.

A typical dosage might range from about 0.001 mg/k/g to about 1,000 mg/k/g, preferably from about 0.01 mg/k/g to about 100 mg/k/g, and more preferably from about 0.10 mg/k/g to about 20 mg/k/g. Advantageously, the compounds of this invention may be administered several times daily, and other dosage regimens may also be useful.

In practicing the methods described herein, the polymer-therapeutic agent combinations may be used alone or in combination with other therapeutic or diagnostic agents. The compounds of this invention can be utilized in vivo, ordinarily in mammals such as primates such as humans, sheep, horses, cattle, pigs, dogs, cats, rats and mice, or in vitro.

An advantage of using the radiopaque, bioresorbable polymers described herein in therapeutic agent delivery applications is the ease of monitoring release of a therapeutic agent and the presence of the implantable therapeutic delivery system. Because the radiopacity of the polymeric matrix is due to covalently attached halogen substituents, the level of radiopacity is directly related to the residual amount of the degrading therapeutic agent delivery matrix still present at the implant site at any given time after implantation. In preferred embodiments the rate of therapeutic release from the degrading therapeutic delivery system will be correlated with the rate of polymer resorption. In such preferred embodiments, the straight-forward, quantitative measurement of the residual degree of radio-opacity will provide the attending physician with a way to monitor the level of therapeutic release from the implanted therapeutic delivery system.

The following non-limiting examples set forth herein below illustrate certain aspects of the invention. All parts and percentages are by mole percent unless otherwise noted and all temperatures are in degrees Celsius unless otherwise indicated. All solvents were HPLC grade and all other reagents were of analytical grade and were used as received, unless otherwise indicated.

EXAMPLES

Example 1

Synthesis of L-tyrosine-N-[2-(4-hydroxyphenoxy)-1-oxoethyl]ethyl ester (PTE)

Into a 1 L round-bottomed flask were added 16.8 g (0.100 mol) (4-hydroxyphenoxy)acetic acid (HPA), 24.6 g (0.105 mol) tyrosine ethyl ester hydrochloride (TE.HCl), 1.35 g (0.01 mol) 1-hydroxybenzotriazole and 150 mL tetrahydrofuran (THF). The contents of the flask were stirred while cooling to 5° C. using ice-water bath. To the stirred mixture was added 10.6 g (0.105 mol) of triethylamine followed by 21.1 g (0.110 mol) of N-(3-Dimethylaminopropyl)-N'-ethyl-carbodiimide hydrochloride (EDCI). This was stirred at 5° C. for 1 and then at room temperature for 5 h.

To the reaction mixture was then added 450 mL of 0.2 M HCl and stirred for 5 min and allowed to stratify. The aqueous layer was removed by siphoning and discarded. To the organic layer was added 150 mL of HCl, stirred for five minutes, allowed to stratify and the organic layer removed and discarded. The procedure was repeated with 150 mL of 5% sodium bicarbonate solution and then stirred with 250 mL of deionized water until the product solidified. The product was isolated by filtration and dried in vacuum oven at 40° C. for 24 h. The $^1$H-NMR spectrum (300 MHz, DMSO-d6) was as follows: δ 9.23 (s, 1H, phenol), 8.98 (s, 1H, phenol), 8.19 (d, J=7.9, 1H, amide), 6.98 (d, J=8.4, 2H, aryl), 6.77-6.59 (m, 6H, aryl), 4.46 (d, J=5.8, 1H, α-proton), 4.35 (s, 2H, —O—CH2-HPA), 4.06 (q, J=7.1, 2H, —O—CH2-), 2.92 (t, J=6.7, 2H, —CH2-), 1.24-1.05 (m, 3H, —CH3). The melting point was 132-135° C.

Example 2

L-Tyrosine-N-[2-(4-hydroxyphenoxy)-1-oxoethyl]-hexyl ester, PTH

PTH was synthesized using procedures similar to that for PTE except in this case 26.5 g (0.105 mol) tyrosine hexyl ester (TH) was used instead of TE.HCl and triethylamine was omitted. Yield: 79 mol %, MP=94-97° C. $^1$H-NMR (300

MHz, DMSO-d6) δ 9.23 (s, 1H, phenol), 8.97 (s, 1H, phenol), 8.19 (d, J=7.9, 1H, amide), 6.97 (d, J=8.4, 2H, aryl), 6.76-6.60 (m, 6H, aryl), 4.54-4.40 (m, 1H, α-proton), 4.34 (s, 2H, —O—CH2-HPA), 4.08-3.94 (m, 2H, —O—CH2-), 3.01-2.83 (m, 2H, —CH2-), 1.49 (dd, J=13.2, 6.5, 2H, —CH2-), 1.35-1.14 (m, 6H, —CH2-), 0.85 (t, J=6.7, 3H, —CH3).

Ex. 3

3,5-Diiodo-L-tyrosine-N-[2-(4-hydroxyphenoxy)-1-oxoethyl]ethyl ester (PI$_2$TE)

PI$_2$TE was synthesized using procedures similar to that for PTH except in this case 48.4 g (0.105 mol) 3,5-diiodo-tyrosine ethyl ester (I$_2$TE) was used instead of TH. In this case the I$_2$TE did not completely dissolve in the solvent and the reaction was carried out in suspension. The $^1$H-NMR spectrum (400 MHz, DMSO-d6) was as follows: δ 9.34 (s, 1H, phenol), 8.96 (s, 1H, phenol), 8.32 (d, J=7.9, 1H, amide), 7.60 (s, 2H, aryl-I$_2$TE), 6.74-6.63 (m, 4H, aryl-HPA), 4.44 (d, J=5.8, 1H, α-proton), 4.35 (s, 2H, —O—CH2-HPA), 4.06 (q, J=7.1, 2H, —O—CH2-), 2.92 (t, J=6.7, 2H, —CH2-I$_2$TE), 1.24-1.05 (m, 3H, —CH3).

Example 4

PI$_2$TE-PHMC12k

Into a 1 L 4-necked round-bottomed flask equipped with a mechanical stirrer, a syringe pump, and a thermometer are added 20 g of PI$_2$TE and 5 g (20 weight percent) of poly(hexamethylenecarbonate)-diol (Mn=12,000), which is prepared according to the method of Example 6 of WO 10/42918, and which is incorporated by reference in its entirety. To the flask are then added 150 mL of methylene chloride and 10.3 mL of pyridine. On stirring a clear solution should result to which a solution of 4.4 g of triphosgene in 17 mL of methylene chloride is added over a period of 2-3 hours using a syringe pump. After the addition is complete the reaction mixture is stirred for 15 min. The resulting viscous solution is quenched with a mixture of 15 mL of THF and 1.5 mL of water. After 15 min the quenched reaction mixture is precipitated with 250 mL of 2-propanol in a 1 L laboratory blender. The resulting oily precipitate is solidified by repeatedly grinding with 2-propanol in the blender. The product obtained in the form of powder is dried in a vacuum oven at 40° C. to constant weight. The resulting PI$_2$TE15 PHMC12k polymer is characterized by its glass transition temperature and NMR spectrum. As indicated by the aforementioned designation "I$_2$DTE-PHMC12k", polymers containing PHMC may be referred to herein in a manner similar to that described above for polymers containing PCL.

Example 5

PI$_2$TE-HDAT12k Polymer

Into a 1 L 4-necked round-bottomed flask equipped with a mechanical stirrer, syringe pump, and a thermometer are added 20 g PI$_2$TE (90 wt. %) and 2.22 g (10 wt. %) poly(HDAT carbonate)-diol (Mn=19,000)) which is prepared according to the method of Example 9 of WO 10/42917, which is incorporated by reference in its entirety. To the flask are then added 180 mL of methylene chloride and 10.2 mL of pyridine. On stirring a clear solution should result to which a solution of 3.8 g of triphosgene in 12 mL of methylene chloride is added over a period of 2-3 hours using a syringe pump. After the addition is complete the reaction mixture was stirred for 15 min. The resulting viscous solution is quenched with a mixture of 15 mL of THF and 1.5 mL of water. After 15 min the quenched reaction mixture is precipitated with 250 mL of 2-propanol in a 1 L laboratory blender. The resulting oily precipitate is solidified by repeatedly grinding with 2-propanol in the blender. The product obtained in the form of powder is dried in a vacuum oven at 40° C. to constant weight.

Example 6

PI$_2$TE-PCL10k-PCL1.25k Polymer

Into a 1 L 4-necked round-bottomed flask equipped with a mechanical stirrer, syringe pump, and a thermometer are added 20 g PI$_2$TE (85 wt. %), 1.89 g (8 wt. %) PCL-10000 and 1.65 g (7 wt. %) PCL-1250. To the flask are then added 133 mL methylene chloride and 26.5 mL pyridine. On stirring a clear solution should result to which a solution of 3.8 g triphosgene in 12 mL methylene chloride is added over a period of 2-3 hours using the syringe pump. After the addition is complete the reaction mixture is stirred for 15 min. The resulting viscous solution is stirred with 200 mL of water and the layers are allowed to separate. The top layer is separated and discarded. The bottom layer is precipitated with 220 mL of 2-propanol in a 1 L laboratory blender. The resulting oily precipitate is repeatedly ground with 2-propanol in the blender until it hardens. The I$_2$DTE-PCL10k-PCL1.25k polymer product obtained in the form of powder was dried in a vacuum oven at 40° C. to constant weight.

Example 7

PI$_2$TE-PCL10k-PCL1.25k Polymer

A PI$_2$TE-PCL10k-PCL1.25k polymer is prepared as described in Example 6 using PI$_2$TE, PCL-10000 and PCL1250, except that the reaction mixture is filtered using a 40-60 micron fitted glass funnel. Precipitation of filtrate and further work up is carried out in a particle-controlled environment. The mechanical properties of the resulting PI$_2$TE-PCL10k-PCL1.25k polymer are compared to a corresponding polymer not prepared under particle-controlled conditions (example 6).

Example 8

Monoester of propane-diol with I$_2$PTE (I2PTE-prD)

Into a 250 mL round-bottomed flask Is added 14.4 g (190 mmol) 1,3-propanediol, 37.9 mmol I$_2$PTE, 1.44 g (7.60 mmol) PTSA and 150 mL chloroform. The flask is equipped with a modified Dean-Stark trap used with solvents heavier than water. The contents of the flask are refluxed while stirring with a magnetic stirrer. The reaction is continued until the expected amount of water (about 0.8 mL) collected. The reaction mixture is evaporated to dryness and then stirred with 100 mL 5% NaHCO$_3$ soln. for 10 min and the aqueous layer is removed. This is repeated a total of 3 times followed by a wash with 100 mL deionized water. The product is isolated by filtration, washed with water, and dried in vacuum oven at 40° C.

Example 9

Esterification of I$_2$PTE-PrD with HPA (I$_2$PTE-PrD-HPA)

Into a 500 mL round-bottomed flask equipped with an overhead stirrer, a Dean-Stark trap and a thermometer are added 19 g (0.04 mol) of 1,3-propanediol, 13.6 g (0.081 mol) of (4-hydroxyphenoxy)acetic acid (HPA), 0.76 g (4.0 mmol) of PTSA, and 200 mL of heptane. The flask is heated using a heating mantle, while stirring with the overhead stirrer so that heptane and water distilled over into the Dean-Stark trap. Heating is continued until water collection stops (about 1.45 mL water should be collected). The reaction mixture is allowed to cool and the supernatant is removed by decantation. The product is collected, dried and purified by recrystallization from a suitable solvent.

Example 9

Esterification of 1,3-propanediol with HPA (P-PrD-P)

Into a 500 mL round-bottomed flask equipped with an overhead stirrer, a Dean-Stark trap and a thermometer are added 3.04 g (0.040 mol) of 1,3-propanediol, 13.6 g (0.081 mol) of (4-hydroxyphenoxy)acetic acid (HPA), 0.76 g (4.0 mmol) of PTSA, and 200 mL of heptane. The flask is heated using a heating mantle, while stirring with the overhead stirrer so that heptane and water distilled over into the Dean-Stark trap. Heating continues until water collection stops (about 1.45 mL water should be collected). The reaction mixture is allowed to cool and the supernatant is removed by decantation. The product is collected, dried and purified by recrystallization from a suitable solvent.

Example 10

Polymerization of (I$_2$DAT-PrD-HPA)) with PCL

Into a 1 L 4-necked round-bottomed flask equipped with a mechanical stirrer, an addition funnel, and a thermometer are added 10 g purified I$_2$DAT-PrD-HPA (85 wt. %), 0.94 g polycaprolactone-diol (Mn=10,000) (8 wt. %) and 0.82 g (7 wt.) polycaprolactone-diol (Mn=1250). To the flask are then added 68 mL methylene chloride and 5.3 mL pyridine. On stirring a clear solution should result to which a solution of 1.86 g triphosgene in 5.2 mL methylene chloride is added over 2-3 h using the addition funnel. A polymer solution is allowed to stir for 15 min. The polymer solution is quenched by the addition of a mixture of 6.1 mL THF and 0.7 mL water. After 15 min the quenched reaction mixture is precipitated with 120 mL 2-propanol in a 1 L laboratory blender. Resulting oily precipitate is repeatedly ground with 2-propanol in the blender to harden it. The product obtained in the form of powder is dried in a vacuum oven at 40° C. to constant weight.

Using similar procedures and replacing PCL-diol of Mn 10,000 with PCL-diols of Mn=3,000, 5,500, and 8,500 three additional copolymers were prepared.

Example 11

Polymerization of (I$_2$DAT-PrD-HPA)) with PCL

A (I$_2$DAT-PrD-HPA)-PCL10k-PCL1.25k polymer is prepared as described in Example 10 using (I$_2$DAT-PrD-HPA), PCL-10000, and PCL1250, except that the reaction mixture is filtered using a 40-60 micron fritted glass funnel. Precipitation of filtrate and further work up is carried out in a particle-controlled environment. The mechanical properties of the resulting (I$_2$DAT-PrD-HPA)-PCL10k-PCL1.25k polymer are compared to a corresponding polymer not prepared under particle-controlled conditions (example 11).

Example 12

Preparation of I$_2$PTE di-ester of 1,5-pentane diol

In a 500 mL flask equipped with overhead stirrer and a Dean-stark trap were placed 1,5-pentane diol (8.75 g, 84 mmol), I$_2$PTE (0.17 mol), 4-toluenesulfonic acid (1.6 g, 8.4 mmol) and 200 mL of heptane. A nitrogen inlet adopter is placed on top of the condenser to maintain nitrogen atmosphere. The flask was heated using a heating mantle. The water collected is periodically measured and the reflux continued until the theoretical amount of water collected. More water than expected may be collected due to water present in the reagents. The reaction is stopped when the water evolution stopped (The heptane turned pink to purple due to trace quantities of iodine liberated). The reaction mixture is allowed to cool with stirring. The crude product is collected by filtration. For purification the crude is dissolved in 100 mL of acetone. To the solution is added with stirring 400 mL 5% NaHCO$_3$ solution and stirring is continued until product crystallizes. The product is collected by filtration and washed with 50 mL of 5% NaHCO$_3$ solution followed by 2×50 mL of DI water. The product is dried in a vacuum oven and characterized by $^1$H NMR and HPLC. Similar procedures are used to prepare I$_2$PTE diesters of hexane diol and propane diol.

Example 13

Preparation of Poly(I$_2$PTE-LA)

In a 100 mL round-bottomed flask are placed 0.012 mol 3-(3,5-diiodo-4-hydroxyphenoxy)acetic acid (HPA)) propionic acid, 2.16 g (0.02 mol) lactic acid, 1.41 g (0.008 mol) dimethylaminopyridinium p-toluenesulfonate (DPTS) and 50 mL methylene chloride. The contents of the flask are stirred under nitrogen and N,N'-diisopropylcarbodiimide (15 g, 0.12 mol) is added to the flask. The reaction mixture is stirred for 24 h under nitrogen. The reaction is stopped and the reaction mixture is filtered through a fritted glass funnel. The residue (diisopropyl urea) is discarded. The filtrate is precipitated with 250 mL isopropanol in a high speed blender, and triturated twice with 50 mL isopropanol. The precipitate is isolated and dried and dried in a vacuum oven. The polymer is characterized by $^1$H NMR, and GPC.

Example 14

Preparation of Low Molecular Weight PLLA-Diol

In a 100 mL round bottom flask were placed 1,3-propanediol (1.02 g, 13.4 mmol), L-lactide (36.3 g, 252 mmol) and stannous octoate (0.5 g, 1.26 mmol). The contents of the flask were stirred and dried under vacuum. The flask was then lowered into a silicon oil bath whose temperature was maintained between 130-140° C. The lactide began to melt and a clear liquid resulted. When observed after 2 h the reaction mixture was opaque (white), still liquid at ca 130° C. The mixture was allowed to react for 24 h. On cooling a white solid was obtained. The $^1$H NMR showed the absence of unreacted 1,3-propane-diol. GPC with THF as mobile phase showed a bi-modal peak with a polystyrene equivalent Mn=3800; and Mw=7500.

Example 15

Polymerization of PLLA-Diol Using Triphosgene

Into a 250 mL round bottomed flask were added 7.50 g (0.005 mol) of PLLA-diol (Mn 1500). To the flask were also added 60 mL methylene chloride and 1.53 g (0.019 mol) pyridine and stirred with an overhead stirrer. To the resulting clear solution was slowly added over a period of 2 h, 0.42 g (0.006 equivalent of phosgene) triphosgene in 2 mL of methylene chloride, using a syringe pump. After stirring for 15 minutes, GPC showed a MW of 60,000. The reaction mixture was washed twice with 0.2 M HCl and precipitated with methanol. The initially formed viscous oil solidified after stirring for 1 hour into a white crystalline solid. This was dried in a vacuum oven at 40° C. for 24 h.

Example 16

Preparation of Iodinated PLLA-Diphenol with $I_2$PTE

In a 250 mL round bottomed flask equipped with a Dean-Stark trap are placed PLLA-diol (8.5 g, 5.0 mmol), I2PTE (11 mol), 4-toluenesulfonic acid (0.1 g, 0.5 mmol) and toluene (125 mL). The reaction mixture is stirred using a magnetic stirrer and heated to reflux for 18 h. About 0.2 mL water collects in the Dean-Stark trap. The reaction mixture is allowed to cool and evaporate to dryness. The residue is dissolved in 50 mL acetone. To this solution is added with stirring 200 mL 5% NaHCO3 solution and continued to stir for 1 h. The solid is isolated by filtration and washed with 50 mL 5% NaHCO3 solution and 2×50 mL Deionized water. The product is dried in a vacuum oven at 40° C.

Example 17

Preparation of Poly(PHMC2K carbonate)

In a 1 L 4-necked flask with overhead stirrer were placed 53.4 g (27 mmol) poly(hexamethylene carbonate 2000) (PHMC2K), 200 mL methylene chloride and 8.23 g (0.104 mol) pyridine. A clear solution formed on stirring. In a 20 mL sample bottle 2.33 g (24 mmol of phosgene) of triphosgene was dissolved in 8 mL of methylene chloride and added to the reaction flask over 2 h using the syringe pump. The reaction mixture was stirred for 15 m and then quenched with 250 mL of 9:1 mixture of THF-water. This was precipitated with 1500 mL of methanol in a beaker using overhead stirrer. The precipitate was allowed to settle for 1 hour, after which the supernatant was decanted off and discarded. The gluey precipitate at the bottom was washed with 200 mL methanol with stirring. It was then washed with 200 mL DI water. The residue was transferred to a PTFE dish and dried under vacuum for 24 h at 50° C. (The product became a molten gel during drying and hardened on cooling). DSC showed an mp of 31.5° C.

Example 17

Monoester of propane-diol with $I_2$PTE

Into a 250 mL round-bottomed flask Are added 14.4 g (190 mmol) 1,3-propanediol, (37.9 mmol) $I_2$PTE, 1.44 g (7.60 mmol) PTSA and 150 mL chloroform. The flask is equipped with a modified Dean-Stark trap used with solvents heavier than water. The contents of the flask are refluxed while stirring with a magnetic stirrer. The reaction is continued until the expected amount of water (about 0.8 mL) collected. The reaction mixture is evaporated to dryness and then stirred with 100 mL 5% $NaHCO_3$ soln. for 10 min and the aqueous layer is removed. This was repeated a total of 3 times followed by a wash with 100 mL deionized water. The product is isolated by filtration, washed with water, and dried in vacuum oven at 40° C.

It will be understood by those of skill in the art that numerous and various modifications can be made without departing from the spirit of the present invention. Therefore, it should be clearly understood that the various embodiments of the present invention described herein are illustrative only and not intended to limit the scope of the present invention.

What is claimed is:
1. A biocompatible polymer comprising:
a first repeating unit of Formula (Ia):

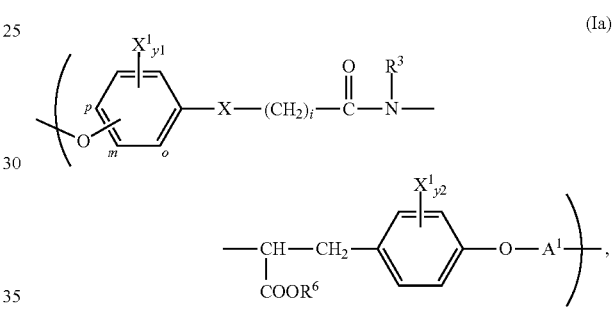

wherein:
i is an integer selected from 1 through 4;
$y^1$ and $y^2$ are each independently selected from 0, 1, 2, 3 and 4;
$X^1$ and $X^2$, at each occurrence, are independently bromine (Br) or iodine (I);
X is oxygen (O), sulfur (S), or $NR^4$; where $R^4$ is selected from the group consisting of hydrogen and alkyl containing from 1 to 6 carbon atoms;
$R^3$ is selected from the group consisting of hydrogen and optionally substituted $C_{1-30}$ alkyl;
$R^6$ is selected from the group consisting of hydrogen, alkyl, aryl, alkylaryl, heteroalkyl and heteroalkylaryl, wherein the non-hydrogen groups contain up to 30 carbon atoms, wherein the heteroalkyl group contains from 1 to 10 heteroatoms independently selected from O, $NR^3$ and S, and wherein the heteroalkylaryl group contains from 1 to 3 heteroatoms independently selected from O, $NR^3$ and S; and
$A^1$ at each occurrence is independently selected from:
a bond,

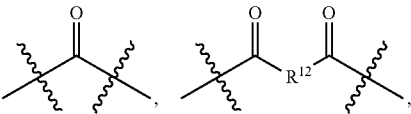

-continued

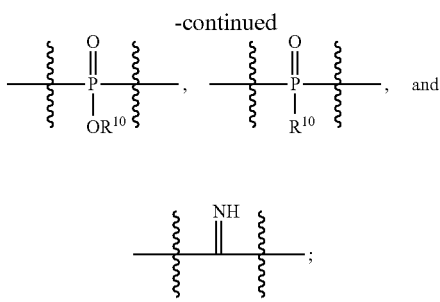

$R^{10}$ is selected from the group consisting of H, $C_1$-$C_{30}$ alkyl, alkenyl, alkynyl, $C_2$-$C_{30}$ heteroalkyl, heteroalkenyl and heteroalkynyl; and $R^{12}$ is selected from the group consisting of a bond, $C_1$-$C_{30}$ alkylene, alkenylene, alkynylene, $C_1$-$C_{30}$ heteroalkylene, heteroalkenylene, heteroalkynylene, $C_5$-$C_{30}$ heteroalkylarylene, heteroalkenylarylene, heteroalkynylarylene, $C_6$-$C_{30}$ alkylarylene, alkenylarylene, alkynylarylene, and $C_5$-$C_{30}$ heteroarylene;

wherein the —$X^1$ and —O— groups on the left phenyl ring, at each occurrence, are independently at o-, m-, or p-positions; and optionally substituted with from one to four substituents independently selected from the group consisting of halogen, halomethyl, halomethoxy, methyl, methoxy, thiomethyl, nitro, sulfoxide and sulfonyl; and $R_1$ is selected from the group consisting of optionally substituted alkylene, heteroalkylene, alkenylene and heteroalkenylene groups containing from one to ten carbon atoms.

2. The biocompatible polymer of claim 1, wherein $X_1$ and $X_2$ of Formula (IIa) are both oxygen atoms.

3. The biocompatible polymer of claim 1, wherein $Ar_1$ is a phenylene ring substituted with two iodine atoms in positions ortho to $X_1$.

4. The biocompatible polymer of claim 1, wherein $R_1$ is an alkylene group containing from one to ten carbon atoms.

5. The biocompatible polymer of claim 1, wherein $A^1$ is a carbonyl having the structure:

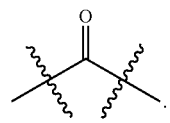

6. A biocompatible polymer comprising:
a first repeating unit of Formula (Ia):

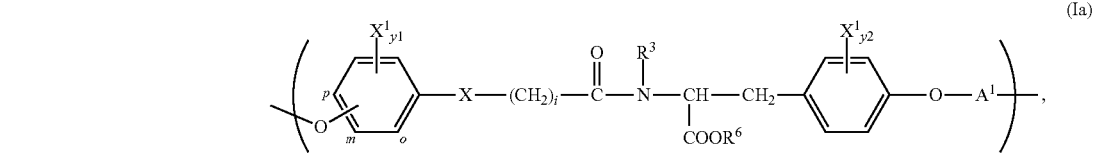

a second repeating unit of Formula (IIa):

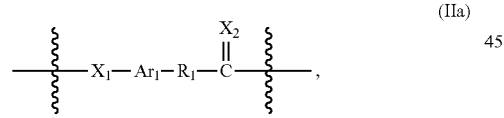

wherein:
$X_1$ and $X_2$ are independently selected from the group consisting of O, S and $NR_3$, wherein $R_3$ is selected from the group consisting of hydrogen and alkyl groups containing from one to 30 carbon atoms;
$Ar_1$ is selected from the group consisting of phenylene,

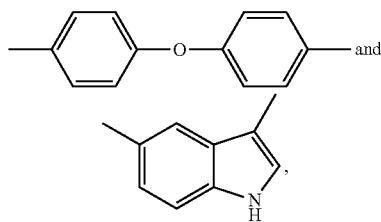

wherein:

i is an integer selected from 1 through 4;

$y^1$ and $y^2$ are each independently selected from 0, 1, 2, 3 and 4;

$X^1$ and $X^2$, at each occurrence, are independently bromine (Br) or iodine (I);

X is oxygen (O), sulfur (S), or $NR^4$; where $R^4$ is selected from the group consisting of hydrogen and alkyl containing from 1 to 6 carbon atoms;

$R^3$ is selected from the group consisting of hydrogen and optionally substituted $C_{1-30}$ alkyl;

$R^6$ is selected from the group consisting of hydrogen, alkyl, aryl, alkylaryl, heteroalkyl and heteroalkylaryl, wherein the non-hydrogen groups contain up to 30 carbon atoms, wherein the heteroalkyl group contains from 1 to 10 heteroatoms independently selected from O, $NR^3$ and S, and wherein the heteroalkylaryl group contains from 1 to 3 heteroatoms independently selected from O, $NR^3$ and S; and $A^1$ at each occurrence is independently selected from:
a bond,

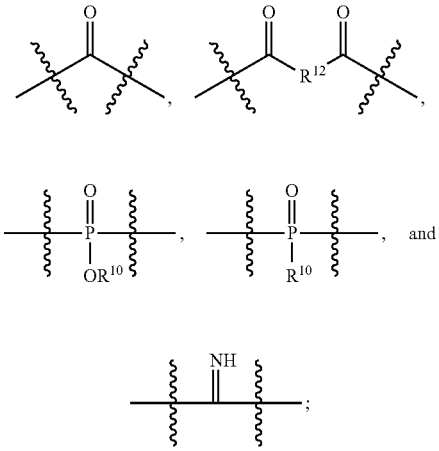

$R^{10}$ is selected from the group consisting of H, $C_1$-$C_{30}$ alkyl, alkenyl, alkynyl $C_2$-$C_{30}$ heteroalkyl, heteroalkenyl and heteroalkynyl; and $R^{12}$ is selected from the group consisting of a bond, $C_1$-$C_{30}$ alkylene, alkenylene, alkynylene, $C_1$-$C_3$ heteroalkylene, heteroalkenylene, heteroalkynylene, $C_5$-$C_{30}$ heteroalkylarylene, heteroalkenylarylene, heteroalkynylarylene, $C_6$-$C_{30}$ alkylarylene, alkenylarylene, alkynylarylene, and $C_5$-$C_{30}$ heteroarylene;

wherein the —$X^1$ and —O— groups on the left phenyl ring, at each occurrence, are independently at o-, m-, or p-positions; and a second repeating unit of Formula (IIIa):

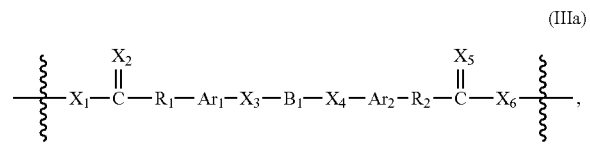

(IIIa)

wherein:

$X_1, X_2, X_3, X_4, X_5,$ and $X_6$ are independently selected from the group consisting of O, S and $NR_3$ wherein $R_3$ is selected from the group consisting of hydrogen and alkyl groups containing from 1 to 30 carbon atoms;

$Ar_1$ and $Ar_2$ are independently selected from the group consisting of phenylene,

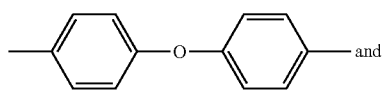 and

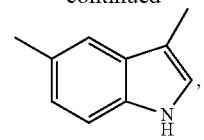

optionally substituted with from one to four substituents independently selected from the group consisting of halogen, halomethyl, halomethoxy, methyl, methoxy, thiomethyl, nitro, sulfoxide, and sulfonyl;

$R_1$ and $R_2$ are independently selected from the group consisting of optionally substituted alkylene, heteroalkylene, alkenylene and heteroalkenylene groups containing from one to ten carbon atoms; and $B_1$ is a carbonyl group.

7. The biocompatible polymer of claim 6, wherein each of $X_1, X_2, X_3, X_4, X_5,$ and $X_6$ is an oxygen atom.

8. The biocompatible polymer according to claim 6, wherein $Ar_1$ and $Ar_2$ are both a phenylene ring substituted with two iodine atoms.

9. The biocompatible polymer according to claim 6, wherein $R_1$ and $R_2$ are each independently alkylene groups containing from one to ten carbon atoms.

10. A block copolymer comprising blocks of the biocompatible polymer according to claim 6, and at least one block derived from a hydroxy endcapped macromer, or at least one block derived from a mercapto endcapped macromer, or at least one block derived from an amino endcapped macromer.

11. The biocompatible polymer of claim 10, wherein said hydroxy endcapped macromer is at least one selected from the group consisting of a hydroxy endcapped poly-caprolactone, a hydroxy endcapped polylactic acid, a hydroxy endcapped polyglycolic acid, a hydroxy endcapped poly(lactic acid-co-glycolic acid), a hydroxy endcapped poly(alkylene diol), a poly(alkylene oxide) and a hydroxy endcapped polydioxanone.

12. The biocompatible polymer of claim 10, wherein the weight ratio of said biocompatible polymer block to the at least one block derived from a hydroxy endcapped macromer is between about 25:75 and about 99:1.

13. The biocompatible polymer of claim 6, comprising at least one repeating unit having the structure (IIIb):

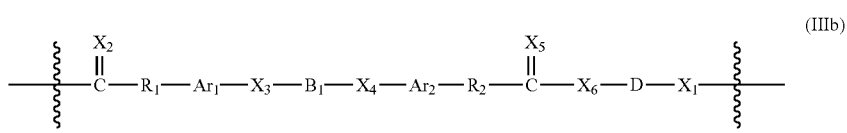

(IIIb)

wherein —$X_6$-D-$X_1$— is derived from H—$X_6$-D-$X_1$—H which is defined as an alkylene diol unit containing up to 24 carbon atoms, an alkylene diamine unit containing up to 24 carbon atoms, an alkylene dimercaptan unit containing up to 24 carbon atoms, a hydroxy endcapped macromer, a mercapto endcapped macromer or an amine endcapped macromer.

14. The biocompatible polymer of claim 13, wherein said hydroxy endcapped macromer comprises at least one selected from the group consisting of a hydroxy endcapped polycaprolactone, a hydroxy endcapped polylactic acid, a hydroxy endcapped polyglycolic acid, a hydroxy endcapped poly(lactic acid-co-glycolic acid), a hydroxy endcapped poly(alkylene diol), a poly(alkylene oxide) and a hydroxy endcapped polydioxanone.

\* \* \* \* \*